US011607229B2

(12) United States Patent
Lavallee et al.

(10) Patent No.: US 11,607,229 B2
(45) Date of Patent: Mar. 21, 2023

(54) SURGICAL SYSTEM FOR CUTTING AN ANATOMICAL STRUCTURE ACCORDING TO AT LEAST ONE TARGET PLANE

(71) Applicant: Orthotaxy, La Tronche (FR)

(72) Inventors: Stéphane Lavallee, Saint Martin d'Uriage (FR); Nicolas Demanget, Saint-Egrève (FR); Hervé Collet, Chatenay (FR); Daniel Girardeau-Montaut, Grenoble (FR); Laurence Chabanas, Crets en Belledonne (FR)

(73) Assignee: Orthotaxy S.A.S., Gières (FR)

( * ) Notice: Subject to any disclaimer, the term of this patent is extended or adjusted under 35 U.S.C. 154(b) by 575 days.

(21) Appl. No.: 16/467,820

(22) PCT Filed: Dec. 7, 2017

(86) PCT No.: PCT/EP2017/081803
§ 371 (c)(1),
(2) Date: Jun. 7, 2019

(87) PCT Pub. No.: WO2018/104439
PCT Pub. Date: Jun. 14, 2018

(65) Prior Publication Data
US 2021/0361295 A1 Nov. 25, 2021

(30) Foreign Application Priority Data
Dec. 8, 2016 (EP) .................................... 16306646

(51) Int. Cl.
*A61B 34/20* (2016.01)
*A61B 17/14* (2006.01)
(Continued)

(52) U.S. Cl.
CPC .......... *A61B 17/155* (2013.01); *A61B 17/157* (2013.01); *A61B 34/20* (2016.02);
(Continued)

(58) Field of Classification Search
CPC ... A61B 2034/305; A61B 34/20–34/37; A61B 17/14–17/142
See application file for complete search history.

(56) References Cited

U.S. PATENT DOCUMENTS 5,236,432 A 8/1993 Matsen et al.
5,620,414 A * 4/1997 Campbell, Jr. .... A61B 17/3203
604/150
(Continued)

FOREIGN PATENT DOCUMENTS

CN 1243690 A 2/2000
CN 101484086 A 7/2009
(Continued)

OTHER PUBLICATIONS

Roth et al., "A New Less Invasive Approach to Knee Surgery Using a Vision-Guided Manipulator", Virtual Reality, Montpellier, France, Dec. 2000, 8 pages.
(Continued)

*Primary Examiner* — Zade Coley
(74) *Attorney, Agent, or Firm* — Condo Roccia Koptiw LLP

(57) ABSTRACT

The invention relates to a surgical system for cutting an anatomical structure (F, T) of a patient according to at least one target plane defined in a coordinate system of the anatomical structure, comprising: i) a robotic device (100) comprising: —a cutting tool, —an actuation unit (4) comprising from three to five motorized degrees of freedom, said actuation unit comprising at least one portion having a
(Continued)

parallel architecture comprising a base (40) and a platform (41) selectively orientable relative to the base (40) according to at least two of said motorized degrees of freedom, —a planar mechanism (24) connecting a terminal part of the actuation unit (4) to the cutting tool (2), ii) a passive articulated lockable holding arm (51) supporting the actuation unit, iii) a tracking unit (200) configured to determine in real time the pose of the cutting plane with respect to the coordinate system of the anatomical structure, iv) a control unit (300) configured to determine the pose of the cutting plane with respect to the target plane, to detect whether the cutting plane can be aligned with one target plane without changing the pose of the actuation unit, the control unit being further configured to, if the cutting plane cannot be aligned with the target plane, compute indication to a user to reposition the actuation unit with respect to the anatomical structure and, if the cutting plane can be aligned with the target plane, control the actuation unit (4) so as to bring the cutting plane into alignment with the target plane, v) a user interface coupled to the control unit, configured to indicate directions to a user to position the actuation unit with respect to the anatomical structure according to a pose allowing aligning the cutting plane with the target plane.

22 Claims, 8 Drawing Sheets

(51) Int. Cl.
  *A61B 17/15* (2006.01)
  *A61B 34/00* (2016.01)
  *A61B 34/30* (2016.01)
  *A61B 90/50* (2016.01)
(52) U.S. Cl.
  CPC .............. *A61B 34/25* (2016.02); *A61B 34/30* (2016.02); *A61B 90/50* (2016.02); *A61B 2034/2051* (2016.02); *A61B 2034/2055* (2016.02); *A61B 2090/508* (2016.02)

(56) References Cited

U.S. PATENT DOCUMENTS

| | | |
|---|---|---|
| 5,748,767 A | 5/1998 | Raab et al. |
| 5,871,018 A | 2/1999 | Delp et al. |
| 6,033,415 A | 3/2000 | Mittelstadt et al. |
| 6,205,411 B1 | 3/2001 | Digioia et al. |
| 6,246,200 B1 | 6/2001 | Blumenkranz et al. |
| 6,322,567 B1 | 11/2001 | Mittelstadt et al. |
| 6,533,737 B1 | 3/2003 | Brosseau et al. |
| 6,554,837 B1 | 4/2003 | Hauri et al. |
| 6,757,582 B2 | 6/2004 | Brisson et al. |
| 6,788,018 B1 | 9/2004 | Blumenkranz et al. |
| 7,035,716 B2 | 4/2006 | Harris et al. |
| 7,206,626 B2 | 4/2007 | Quaid et al. |
| 7,206,627 B2 | 4/2007 | Abovitz et al. |
| 7,346,417 B2 | 3/2008 | Luth et al. |
| 7,747,311 B2 | 6/2010 | Quaid et al. |
| 7,831,292 B2 | 11/2010 | Quaid et al. |
| 8,010,180 B2 | 8/2011 | Quaid et al. |
| 8,095,200 B2 | 1/2012 | Quaid et al. |
| 8,287,522 B2 | 10/2012 | Moses et al. |
| 8,396,598 B2 | 3/2013 | Sutherland et al. |
| 8,460,277 B2 | 6/2013 | Suarez et al. |
| 8,506,555 B2 | 8/2013 | Ruiz et al. |
| 8,518,051 B2 | 8/2013 | Shoham et al. |
| 8,838,205 B2 * | 9/2014 | Shoham .............. A61B 17/1703 600/424 |
| 8,882,777 B2 | 11/2014 | Heavener et al. |
| 9,043,023 B2 | 5/2015 | Noro et al. |
| 9,060,794 B2 * | 6/2015 | Kang .................. A61B 34/30 |
| 9,119,655 B2 | 9/2015 | Bowling et al. |
| 9,149,281 B2 | 10/2015 | Bonutti et al. |
| 9,220,510 B2 | 12/2015 | Cheal et al. |
| 9,226,796 B2 | 1/2016 | Bowling et al. |
| 9,271,804 B2 | 3/2016 | Wu et al. |
| 9,275,192 B2 | 3/2016 | Kang et al. |
| 9,289,264 B2 | 3/2016 | Iorgulescu et al. |
| 9,364,291 B2 | 6/2016 | Bellettre et al. |
| 9,492,237 B2 | 11/2016 | Kang et al. |
| 9,561,082 B2 * | 2/2017 | Yen ........................ G05B 15/02 |
| 9,665,686 B2 | 5/2017 | Van et al. |
| 9,724,165 B2 | 8/2017 | Arata et al. |
| 9,743,936 B2 | 8/2017 | Huet et al. |
| 9,812,035 B2 | 11/2017 | Stuart et al. |
| 9,814,468 B2 * | 11/2017 | Kang ................. A61B 17/1622 |
| 9,827,115 B2 | 11/2017 | Walker et al. |
| 9,901,356 B2 | 2/2018 | Shen et al. |
| 9,937,014 B2 | 4/2018 | Bowling et al. |
| 10,004,565 B2 | 6/2018 | Kang et al. |
| 10,028,789 B2 | 7/2018 | Quaid et al. |
| 10,064,689 B2 | 9/2018 | Swarup et al. |
| 10,105,149 B2 | 10/2018 | Haider et al. |
| 10,383,638 B2 | 8/2019 | Cheal et al. |
| 10,653,488 B2 | 5/2020 | Kang et al. |
| 11,154,369 B2 | 10/2021 | Roldan et al. |
| 11,278,296 B2 | 3/2022 | Otto et al. |
| 2005/0171553 A1 | 8/2005 | Schwarz |
| 2006/0015114 A1 | 1/2006 | Bernardoni et al. |
| 2007/0100258 A1 * | 5/2007 | Shoham ............... A61B 17/157 600/587 |
| 2007/0137372 A1 | 6/2007 | Devengenzo et al. |
| 2007/0156157 A1 | 7/2007 | Nahum et al. |
| 2009/0228145 A1 | 9/2009 | Hodgson et al. |
| 2011/0130761 A1 * | 6/2011 | Plaskos .................. A61B 34/30 606/87 |
| 2012/0143084 A1 * | 6/2012 | Shoham ............. A61B 17/1675 600/567 |
| 2014/0236159 A1 | 8/2014 | Hani et al. |
| 2015/0112344 A1 * | 4/2015 | Shoham ............. A61B 17/1725 606/64 |
| 2015/0182285 A1 * | 7/2015 | Yen ...................... B25J 17/0216 606/80 |
| 2015/0257838 A1 * | 9/2015 | Huet .................. A61B 17/8095 606/80 |
| 2016/0113720 A1 * | 4/2016 | Lavallee ................ A61B 34/70 606/130 |
| 2016/0113728 A1 | 4/2016 | Cameron et al. |
| 2016/0135816 A1 | 5/2016 | Lavallee et al. |
| 2016/0206375 A1 | 7/2016 | Abbasi et al. |
| 2017/0079731 A1 | 3/2017 | Griffiths et al. |
| 2020/0323540 A1 | 10/2020 | Kang et al. |

FOREIGN PATENT DOCUMENTS

| | | | |
|---|---|---|---|
| CN | 101919736 A | 12/2010 | |
| CN | 102778848 A | 11/2012 | |
| CN | 103300906 A | 9/2013 | |
| CN | 103764061 A | 4/2014 | |
| CN | 105050527 A | 11/2015 | |
| CN | 105431102 A | 3/2016 | |
| CN | 106132335 A | 11/2016 | |
| CN | 106132345 A | 11/2016 | |
| CN | 110076774 A | 8/2019 | |
| DE | 102011004370 A1 | 8/2012 | |
| EP | 456103 A2 | 11/1991 | |
| EP | 2529910 A1 | 12/2012 | |
| EP | 3007637 A1 | 4/2016 | |
| JP | 2009-520573 A | 5/2009 | |
| JP | 2016-523614 A | 8/2016 | |
| WO | WO 2004-019785 A2 | 3/2004 | |
| WO | 2007/045810 A2 | 4/2007 | |
| WO | 2007/075864 A1 | 7/2007 | |
| WO | 2012/131658 A1 | 10/2012 | |
| WO | 2012/131660 A1 | 10/2012 | |
| WO | WO-2012131660 A1 * | 10/2012 | ............ A61B 17/86 |
| WO | 2014/198784 A1 | 12/2014 | |
| WO | 2016/126914 A1 | 8/2016 | |

(56) References Cited

FOREIGN PATENT DOCUMENTS

OTHER PUBLICATIONS

Taylor, et al., "An Image-Directed Robotic System for Precise Orthopaedic Surgery", IEEE Transaction on Robotics and Automation, vol. 10, No. 3, Jun. 1994, 15 pages.

Kerschbaumer, et al., "A Mechatronic System for the Implantation of the Acetabular Component in Total Hip Alloarthroplasy", University of Siegen, Hoelderlinstr, 2001, 2 pages.

* cited by examiner

SURGICAL SYSTEM FOR CUTTING AN ANATOMICAL STRUCTURE ACCORDING TO AT LEAST ONE TARGET PLANE

FIELD OF THE INVENTION

The invention relates to a robotic system for cutting an anatomical structure of a patient according to at least one target plane.

BACKGROUND OF THE INVENTION

There are a number of surgical interventions requiring osteotomy, i.e. cutting an anatomical structure such as a bone along a target plane.

Total knee arthroplasty typically requires cutting both the femoral epiphysis and tibial epiphysis in order to remove the damaged bone and cartilage and install a knee prosthesis.

To that end, a surgeon has to carry out five or more cuts on the femur and one or more cuts on the tibia by using an oscillating saw through cutting blocks.

FIG. 1 is a schematic perspective view of a knee intended to receive a knee prosthesis including a femoral component FC and a tibial component TC. Generally, the cuts to be made on the femur F are: a distal cut along plane F1, an anterior cut along plane F2, a posterior cut along plane F3, and anterior and posterior chamfers F4, F5 connecting the distal plane and the anterior, respectively posterior, plane. A cut has been made on the tibia T along plane T1.

In order for the surgeon to carry out all these planes accurately and in a reduced time, computer assisted systems have been developed.

For example, document WO 2014/198784 teaches a surgical system comprising a handheld device that includes:
  a base designed to be held in a user's hand,
  an end-effector for mounting a burr intended to mill a planned volume of a part of a patient's body,
  an actuation unit connected to said base and said end-effector for moving the burr with respect to the base in order to treat said planned volume,
  a support unit connected to the base or to the end-effector which provides a partial mechanical link between the base or the end-effector and the part to be treated.

The system also comprises a tracking unit which is configured to determine in real time the pose of at least one of the burr, the end-effector and the base with respect to the part to be treated.

A control unit of the system is configured to:
  (a) compute in real time an optimized path of the burr or of the end-effector with respect to the base depending on said measured pose,
  (b) detect whether said computed path of the burr or of the end-effector can be achieved without changing the pose of the base, and, if this is not the case, determine a possible repositioning of the base with respect to the part to be treated,
  (c) configure the actuation unit so as to move the end-effector according to said computed path, and
  (d) iterate steps (a) to (c) until the planned volume has been treated.

A user interface is used to indicate feedback information to the user.

However, even if the robot described in this document is very efficient for milling a body part, the design with an actuation unit in the form of a planar five-bar linkage as illustrated in document WO 2014/198784 is not optimal for cutting a body part with a saw. Indeed, such a robot does not allow the user to manipulate the cutting tool, thus depriving the user from his/her usual feeling and freedom when accomplishing the surgical gesture.

Document US 2011/0130761 teaches a robotic system dedicated to guiding a saw in order to carry out several cuts on a femur in total knee arthroplasty. The system comprises a navigation system that locates in position and orientation trackers attached to the bone and instruments.

The system comprises a seat attached to the femur by at least one pin.

An adjustment system comprising two screws is attached to the seat via a ball and socket joint.

The cutting block, which comprises a slot intended to guide a saw blade within a cutting plane, is attached to an arm that supports two motors.

The arm is pivotally mounted on the adjustment system, the orientation of the arm relative to the seat being adjustable by the two screws of the adjustment system.

The arm is rotatable relative to the seat about a first rotation axis by a first motor, the cutting block is rotatable relative to the arm relative to a second rotation axis by the second motor, both rotation axes being parallel to each other.

In use, the seat is fixed to the femur by the at least one pin, then the position of the first and second rotation axes is fixed by the adjustment device which is operated manually by the surgeon, with visual feedback from the navigation system. Once a suitable position has been found, the trackers attached to the cutting block are removed and the cutting block is no longer navigated. Then, the motors are operated to move the cutting block about two rotational axes. The surgeon then cuts the bone along each desired cutting plane using a saw received in the cutting block. At that time, the system is not able to detect or compensate in real time a potential misalignment of the slot of the cutting block relative to the target planes.

A major drawback of such a system is that the fixation of the seat to the femur is quite invasive since it requires implanting large pins into the bone to bear the weight of the robot and compensate for forces exerted during sawing by the saw inserted in the cutting block carried by the robot. Large pins used to carry an important weight and react to important strengths can potentially generate bone fracture. In addition, weight and strengths can lead to motion of the pins in the bone, which will impact significantly the accuracy of the system.

Besides, the rotational axes have to be adjusted very precisely in order to achieve all the target planes. However, this adjustment is difficult and prone to errors or inaccuracy because it is done manually and is only assisted by a visual feedback provided by the navigation system. If the cutting plane slightly moves during sawing because of forces exerted by the user or saw, it would be very difficult for the user to detect it and to correct those adjustments manually.

Moreover, if the pins are not placed in a correct location because of surgical constraints, anatomical constraints, or misuse, the robot will not be able to position the cutting block so that all the cuts can be reached, and it will be necessary to reposition the pins in the bone at a slightly different location, which is difficult.

In addition, this system does not allow carrying out the tibial cut while the seat is fixed to the femur, and therefore another specific device is necessary to perform cuts on the tibia, which takes additional time, additional pins, additional systems and efforts.

BRIEF DESCRIPTION OF THE INVENTION

A goal of the invention is to provide a surgical system intended to guide a surgical saw to cut an anatomical structure of a patient according to at least one target plane, which does not require any invasive attachment to the patient and while controlling precisely the position and orientation of a cutting tool to reach the target plane.

Accordingly, the invention provides a surgical system for cutting an anatomical structure of a patient according to at least one target plane defined in a coordinate system of the anatomical structure, comprising:
(i) a robotic device comprising:
   a cutting tool configured to cut the anatomical structure according to a cutting plane,
   an actuation unit comprising from three to five motorized degrees of freedom, said actuation unit comprising at least one portion having a parallel architecture comprising a base and a platform selectively orientable relative to the base according to at least two of said motorized degrees of freedom, for adjusting a position and orientation of the cutting plane relative to the target plane,
   a planar mechanism connecting a terminal part of the actuation unit to the cutting tool,
(ii) a passive articulated lockable holding arm supporting the actuation unit,
(iii) a tracking unit configured to determine in real time the pose of the cutting plane with respect to the coordinate system of the anatomical structure,
(iv) a control unit configured to determine the pose of the cutting plane with respect to the target plane, to detect whether the cutting plane can be aligned with one target plane without changing the pose of the actuation unit, the control unit being further configured to, if the cutting plane cannot be aligned with the target plane, compute indication to a user to reposition the actuation unit with respect to the anatomical structure and, if the cutting plane can be aligned with the target plane, control the actuation unit so as to bring the cutting plane into alignment with the target plane,
(v) a user interface coupled to the control unit, configured to indicate directions to a user to position the actuation unit with respect to the anatomical structure according to a pose allowing aligning the cutting plane with the target plane.

In the present text, "substantially parallel axes" means axes making an angle between themselves which is 0°±30°.

By "holding arm" is meant an articulated arm made of at least two segments and that can be locked in a given position. The holding arm is attached to a stable structure of the operating room, such as an operating table, a leg holder, or a mobile cart with blocked wheels.

By "actuation unit" is meant a series of rigid segments linked together by motorized degrees of freedom. The actuation unit is rigidly attached to the extremity of the holding arm. The actuation unit is controlled by a control unit.

By "planar mechanism" is meant a mechanism that constrains an object to move only inside a plane, with at least two degrees of freedom. For example, a planar mechanism can be made of two degrees of translation and one degree of rotation.

By "cutting tool" is meant a saw, a burr, a laser, or a high-pressure water jet, that are able to perform cuts in a bone. For knee surgery, the cutting tool is generally made of a power unit that carries and activates an oscillating saw blade.

By "anatomical structure" is meant in the present text a substantially rigid structure, such as a bone or cartilage, or a joint formed of two bones.

By "pose" is meant, in the present text, the 3D position and 3D orientation of a tool in up to six degrees of freedom. It is to be noted that depending on the application, a pose may not be necessarily determined by all six degrees of freedom but by only one degree of freedom or a subset comprising less than six degrees of freedom.

By "alignment" of the cutting plane with a target plane, is meant in the present text that said cutting plane deviates from the target plane by a distance of less than 1 mm and an angle of less than 1°. Preferably, the cutting plane coincides perfectly with the target plane. To measure such a distance, a selected point of the target plane is projected onto the cutting plane, and the distance between the projected point and the target plane is measured. The selected point shall be in the vicinity of the anatomical structure to be cut. For example, the selected point may be an anatomical point of the anatomical structure, or the center of the anatomical structure to be cut, projected on the target plane.

By "partial mechanical link" is meant a mechanical link between at least two parts, wherein a relative movement of said at least two parts in at least one degree of freedom is possible. This term excludes a "complete" mechanical link, i.e. a link wherein no relative movement between the parts is allowed—an example of such complete mechanical link would be rigidly attaching the robotic system to a bone to be cut by at least one screw or pin implanted into said bone.

As described in further detail below, said partial mechanical link provided between the cutting tool and the anatomical structure of the patient's body may be direct, meaning that the support unit is in contact with the structure to be cut itself, or indirect, meaning that the support unit is in contact with a part of the patient's body adjacent to the structure to be cut. Said adjacent part may consist of a bone belonging to the same joint as the structure to be cut, or of soft tissues (possibly including the skin) that surround said structure. An indirect partial mechanical link may also be obtained when the support unit is held by a user's hand and that said hand leans onto the structure to be cut or the soft tissues and skin surrounding the structure to be cut.

Depending on the part with which the support unit makes contact and on the design of the support unit itself, said partial mechanical link may be rigid or damped.

The device is able to compensate for a given amount of pose errors (e.g. due to small movements of the user or involuntary movement of the patient).

According to an embodiment, the cutting tool is a surgical saw comprising a saw blade configured to oscillate within a determined cutting plane.

The cutting plane may be parallel to the plane of the planar mechanism. Alternatively, the cutting plane may be orthogonal to the plane of the planar mechanism.

According to an embodiment, the cutting tool is a burr.

According to an embodiment, the cutting tool is a laser.

According to an embodiment, the cutting tool is a high-pressure water jet.

According to an embodiment, the cutting tool is a scalpel or a lancet or an ultrasonic cutter adapted for cutting soft tissues.

According to an embodiment, the planar mechanism is passive.

According to another embodiment, the planar mechanism is at least partially active. For example, the planar mechanism comprises at least two motorized degrees of freedom.

According to an embodiment, the system further comprises a locking system adapted for locking each degree of freedom of the planar mechanism once the cutting plane has been aligned with the target plane.

Advantageously, the holding arm comprises a braking system configured to apply a braking force inversely proportional to a distance between a current pose of the robotic device and a target pose enabling alignment of the cutting plane with the target plane.

The tracking unit advantageously comprises at least one tracker configured to be rigidly attached to the anatomical structure and at least one tracker rigidly attached to the holding arm and/or to the actuation unit.

Preferably, the tracking unit further comprises a tracker configured to be rigidly attached to the cutting tool.

According to an embodiment, the system further comprises an interface configured for attaching the cutting tool at an end of the planar mechanism, wherein the tracking unit comprises a tracker configured to be rigidly attached to said end of the planar mechanism.

Advantageously, the control unit is configured to allow operation of the cutting tool only when the cutting plane is aligned with the target plane.

According to an embodiment, the system further comprises a support unit connected to the actuation unit and/or the holding arm, comprising at least one element designed to make contact with the anatomical structure to be cut or a region of the patient's body adjacent to the anatomical structure to be cut so as to provide a partial mechanical link between the cutting tool and the anatomical structure to be cut.

Advantageously, the support unit comprises at least two detachable elements, a first element configured to be attached to the anatomical structure and a second element configured to be attached to the actuation unit and/or the holding arm.

The first element may comprise a rigid base and a strap configured to be wrapped around the anatomical structure to maintain the rigid base, said rigid base being configured to be removably attached to the second element.

According to an embodiment the first and second elements of the support unit are lockable, and the system comprises a single actuator for unlocking the holding arm and said first and second elements of the support unit.

According to an embodiment, the control unit is configured to implement a control loop comprising the following steps:
(S1) determining poses of the actuation unit and the anatomical structure using localization information provided by the tracking unit;
(S2) based on a geometrical model of the actuation unit, computing a theoretical pose of the planar mechanism from the poses determined in step (S1), and computing a deviation between the plane of the planar mechanism and the target plane;
if said deviation is less than a threshold, allowing operation of the cutting tool and returning to step (S1) to determine new poses of the actuation unit and of the anatomical structure;
if said deviation is greater than or equal to said threshold,
(S3) projecting the target plane in the coordinate system of the actuation unit;
(S4) computing a new attitude of the actuation unit to align the cutting plane with the target plane, and determining the movements to be applied by the motors of the actuation unit;
(S5) activating the actuation unit to apply said movements, and returning to step (S1) to determine new poses of the actuation unit and of the anatomical structure.

According to an alternative embodiment, when a tracker is attached to the cutting tool or to the interface connecting the cutting tool to the planar mechanism, the control unit is configured to implement a control loop comprising the following steps:
(S'1) determining poses of the actuation unit, the cutting tool and the anatomical structure using localization information provided by the tracking unit;
(S'2) computing a deviation between the cutting plane and the target plane;
if the deviation is less than a threshold, allowing operation of the cutting tool and returning to step (S'1) to determine a new pose of the actuation unit, cutting tool and anatomical structure;
if the deviation is greater than or equal to the threshold, projecting (S'3) the cutting plane and the target plane in the coordinate system of the actuation unit,
(S'4) computing a transformation between the plane of the planar mechanism and the cutting plane;
(S'5) updating the target plane with the transformation computed in step (S'4);
(S'6) computing a new attitude of the actuation unit to align the cutting plane with the updated target plane, and determining the movements to be applied by the motors of the actuation unit;
activating the actuation unit to apply said movements.

According to an embodiment, the user interface is configured to display a representation of the anatomical structure to be cut, a line representing the target plane and a line representing the cutting plane according to two different views, wherein indicators in the form of a pair of bars have a determined length such that the line representing the cutting plane intersects both bars in each view only if the cutting plane can be aligned with the target plane.

BRIEF DESCRIPTION OF THE DRAWINGS

Other features, embodiments and advantages of the invention will be apparent from the detailed description that follows, based on the appended drawings wherein.

DETAILED DESCRIPTION OF EMBODIMENTS OF THE INVENTION

The following description is focused on surgery requiring at least one osteotomy step.

The invention can be applied to various applications where there is a need to perform cuts along at least one plane in a bony anatomy. In particular but not limitatively, the invention could be implemented in the following surgical applications: total knee arthroplasty (TKA) (in which case the anatomical structure to be cut is a joint formed of the femur and the tibia), partial knee arthroplasty including unicompartmental knee arthroplasty (UKA), bicompartmental knee arthroplasty, patellofemoral knee arthroplasty, tibial or femoral osteotomy, patella resurfacing, hallux valgus surgery, hip surgery for cutting the proximal femur, shoulder surgery for cutting the humeral head, spine surgery for correcting deformities and performing an osteotomy of the vertebral body, ankle surgery, maxillofacial surgery.

As will be explained in further detail below, the device is used in a context in which at least one target plane along which the anatomical structure has to be cut is planned before performing the cut(s).

Planning of at least one target plane is performed using pre-operative images (e.g. CT, MRI, Ultrasound images, 2D or 3D X-rays in combination with statistical shape models, PET, etc.) or intra-operative 3D data (e.g. intra-operative CT or CBCT, intra-operative MRI, Ultrasound images, 2D or 3D intra-operative X-ray images, geometric data provided by localizing systems and providing 3D points, clouds of 3D points, surfaces reconstructed from clouds of 3D points, etc.), or both.

Multiple computer-assisted surgery methods exist to register the target plane with a coordinate system attached to the anatomical structure to be cut, using images or geometric patient data collected during surgery.

Typically, intra-operative images or data are used to register pre-operative images in a unique coordinate system attached to the anatomical structure, and usually represented by a tracker that can use any of computer assisted surgery technologies (optical tracker made of reflective markers, optical tracker made of active LEDs, electromagnetic trackers made of coils, combination of inertial sensors, ultrasonic sensors, RFID sensors, etc.).

Using any of these conventional computer-assisted surgery methods results in that the target planes have a known geometric representation in a coordinate system attached to the anatomical structure to be cut, and whose movements are tracked in real-time by a tracking unit as it will be detailed below. Typically, the surgical planning step for total knee surgery results in five target planes defined in a coordinate system attached to a tracker fixed to the femur and one target plane defined in a coordinate system attached to a tracker fixed to the tibia.

Figure 1:
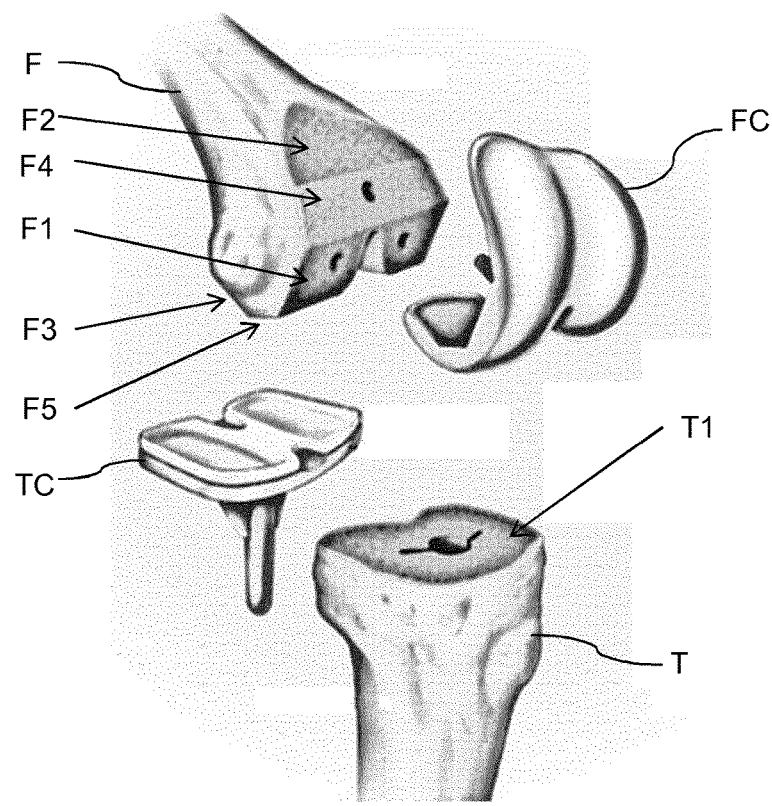
FIG. 1 schematically illustrates the cuts to be made into a femur and a tibia in order to implant a knee prosthesis.
Figure 2:
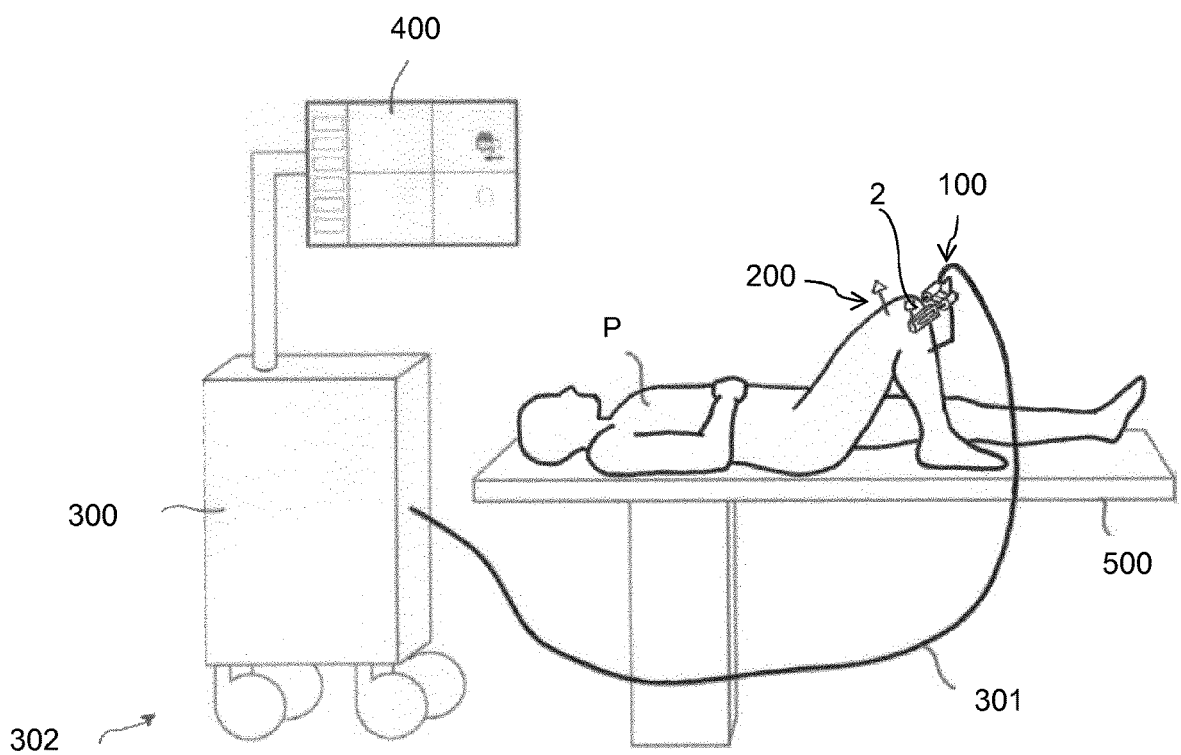
FIG. 2 shows an overview of a surgical system according to the invention.

FIG. 2 shows an overview of a surgical system according to the invention.

A patient P is lying on an operating table 500, e.g. in view of total knee arthroplasty (TKA).

To that end, a cutting tool, such as a saw which is intended to cut the tibial and femoral bones along at least one target plane is used by a user such as a surgeon. Said cutting tool comprises a saw blade.

A cutting tool 2 which may comprise a saw blade constrained within a determined cutting plane is supported by a robotic device 100 that is manipulated by a user such as a surgeon (not shown).

The cutting tool is held by the robotic device 100 and is constrained in each target plane by an actuation unit 4 (not shown in FIG. 2, but better seen in subsequent drawings).

The robotic device 100 is connected to a control unit 300 that controls the actuation unit.

Said control unit typically comprises power supply, AC/DC converters, motion controllers to power the motors of the actuation unit, fuses, real-time control system interface circuits.

The system also comprises a tracking unit 200, such that the relative pose of the device and the anatomical structure to be cut is tracked in real time and is shared between a real time control unit and a planning system.

At least one coordinate system is attached to the anatomical structure while at least one coordinate system is attached to the cutting tool and/or the robotic device.

The tracking unit measures the relative motions between both coordinate systems in real time. Real time means high frequencies greater than twenty Hertz, preferably in the range of one hundred to five hundred Hertz, with low latency, ideally less than five milliseconds.

The data obtained by the tracking unit are transferred to the control unit 300 via any suitable connection, with wires 301 or wireless, with low latency.

The real time control unit is able to carry out the proposed real time control algorithms at a reasonably high frequency with low additional latency.

The real time control unit computes in real time the position of the saw with respect to a target plane depending on said measured pose.

In this figure, the connection is represented by a wire 301 but it may instead be wireless if the robotic device is battery-powered.

The control unit and tracking unit may be arranged in a cart 302 that can be moved in the operating room. They can be also mounted on separate carts, articulated holding arms, lighting systems, or the tracking unit can be also mounted directly on the anatomical structure or on some parts attached to the robotic device. For example, the cutting tool can rigidly support an electromagnetic emitter while electromagnetic sensors can be attached to the anatomical structure.

The system may also comprise a visual user interface 400 that is intended to display feedback information to a user and enable system configuration by the user. The feedback information may comprise:
- indication about a deviation (distance and/or angle) between the cutting plane and the target plane, before the anatomical structure is cut;
- indication about whether the target plane can be achieved with the current position of the robotic device;
- directions to reposition the robotic device with respect to the anatomical structure to be cut in order to align the cutting plane with the target plane;
- real time information about the alignment of the cutting plane with the target plane while the anatomical structure is being cut.

Said user interface 400 may advantageously comprise a screen, which may be located on a cart in the operating room, e.g. on the same cart 302 as the control unit and tracking unit, or on a separate cart, or attached to the walls or the ceiling of the operating room.

In addition to or instead of said screen, the user interface may comprise an indicator that is arranged on the robotic device itself to provide information to the user. Said indicator can be made of LEDs arranged to indicate arrows, numbers or letters, or a miniature display.

A surgical system wherein the control unit, tracking unit and/or user interface are embedded in the robotic device itself would still be within the scope of the invention, provided that the embedded units are powered by a sufficiently powerful power supply or battery and that their size and weight do not hinder the manipulation of the robotic device by the user. For example, micro cameras can be attached to the base of the actuation unit and markers can be attached to the anatomical structure and to the cutting tool.

Before cutting the anatomical structure, the user plans the intervention on the planning system, based on pre-operative and/or intra-operative medical images and data.

This planning step allows determining each target plane suited to perform the cut of the anatomical structure. It is specific to each application.

For example, as already described above, in the case of TKA, planning the implantation of a prosthesis on a knee usually results in the definition of five target planes on the femur and one on the tibia.

The planning system may form part of the surgical system according to the invention; otherwise, the planning system may be provided separately and connected to the control unit.

During the surgical intervention, the user may either use preoperative data/images together with intra-operative registration methods, or use directly intraoperative data/images.

In both cases, the result of the planning consists of at least one target plane, the pose of each plane being determined in the coordinate system of the anatomical structure to be cut.

The pose of each target plane is then transferred to the control unit.

The control unit initializes its sub-systems and the device is ready to use.

Before operation of the device starts, the support unit has to be connected to the anatomical structure to be cut or an adjacent region of the patient's body to provide a partial mechanical link between the cutting tool and the anatomical structure.

Once operation of the device has been started by the user, the control unit continuously feeds back status and tracking information to the control unit for recalculation and visualization purposes.

During use of the device, the user is provided with information regarding repositioning of the robotic device to be carried out in order for the actuation unit to be able to align the cutting plane of the cutting tool with a target plane.

The partial mechanical link provided by the support unit enables the user to make small movements to reposition the device, or allows compensating involuntary motion of the patient, without any additional invasive action on the patient.

According to an embodiment, the cutting tool is a surgical saw attached to the actuation unit using a planar mechanism. The saw 2 comprises a casing 23 and a saw blade 22 that oscillates in a determined plane (called "cutting plane") relative to the casing 23 (see in particular FIGS. 3-5). Thus, the saw blade can be operated to cut the anatomical structure according to a target plane without requiring any cutting block, provided that the actuation unit 4 constrains the saw in the target plane in real time. Usually, the cutting plane is parallel to the longitudinal axis of the casing and the saw blade oscillates on both sides of this axis; such a saw is known in the medical field as a "sagittal saw". The casing is usually positioned relative to the planar mechanism so that the cutting plane is parallel to the plane of the planar mechanism.

According to an embodiment, the saw blade moves back and forth along the longitudinal axis of the casing; such a saw is known in the medical field as a «reciprocating saw». The casing is usually positioned relative to the planar mechanism so that the cutting plane is orthogonal to the plane of the planar mechanism.

According to an embodiment (not illustrated), the cutting tool is a burr. Indeed, especially if the burr tip is small (e.g. with a diameter of the order of three mm), the operation of the burr constrained in a cutting plane allows performing a planar cut. The burr tip can be spherical or cylindrical. Typically a cylindrical shape burr tip with a three mm diameter constrained by the planar mechanism to remain in a plane parallel to the cylinder axis will be rigid enough to make large cuts and small enough to perform fast cutting.

According to an embodiment (not illustrated), the cutting tool is a laser with a system to control the depth of penetration of the laser to avoid damaging soft tissues behind the bone.

According to another embodiment (not illustrated), the cutting tool can be a high-pressure water jet or any other device that creates cuts in an anatomical structure.

According to another embodiment, for cutting soft tissues, the cutting tool can be a scalpel or any electrically activated device such as a lancet or an ultrasonic cutter.

In the drawings that are described below, the cutting tool is usually a saw, without any intended limitation of the invention.

Figure 3:
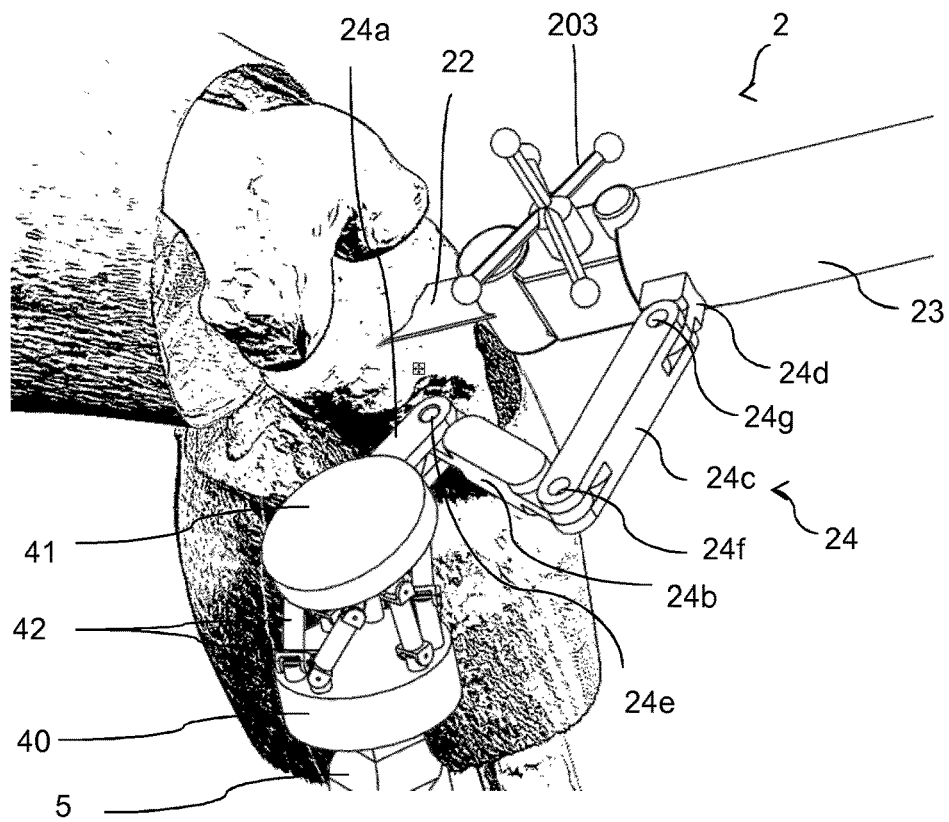
FIG. 3 shows a robotic device according to an embodiment of the invention while performing a tibial cut.

As shown in FIG. 3, the actuation unit 4 has a parallel architecture that comprises a base 40 and a platform 41 that can be selectively oriented relative to the base. To that end, the platform 41 is linked to the base 40 by a plurality of links each providing a degree of freedom in rotation, and if appropriate, also in translation. The actuation unit 4 comprises motors, gears and sensors connected together to form a kinematic structure. These components are integrated in an optimal way such that the robotic device remains as compact and light as possible.

In the embodiment of FIG. 3, the actuation unit is represented as a hexapod, with six legs 42 connecting the base 40 to the platform 41, each end of the legs 42 being pivotally coupled to the base and the platform, respectively.

However, any other structure, usually designated by the term "parallel architecture", with a platform selectively orientable relative to a base, could be used without departing from the scope of the present invention. Hexapods and other parallel architectures are known in particular in the medical field, for example under the names Hayward wrist, Agrawal wrist, Gosselin's agile eye, Tesar wrist, Cheng wrist, etc., and do not need to be described in more detail.

Figure 4:
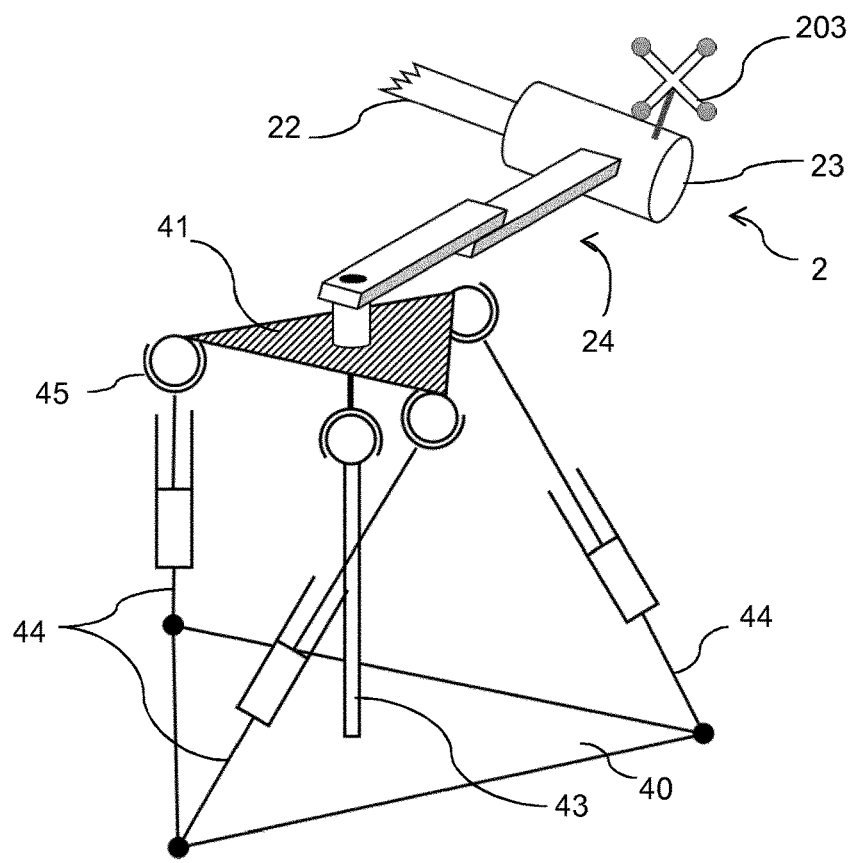
FIG. 4 shows a schematic representation of an embodiment of a parallel architecture.
Figure 5:
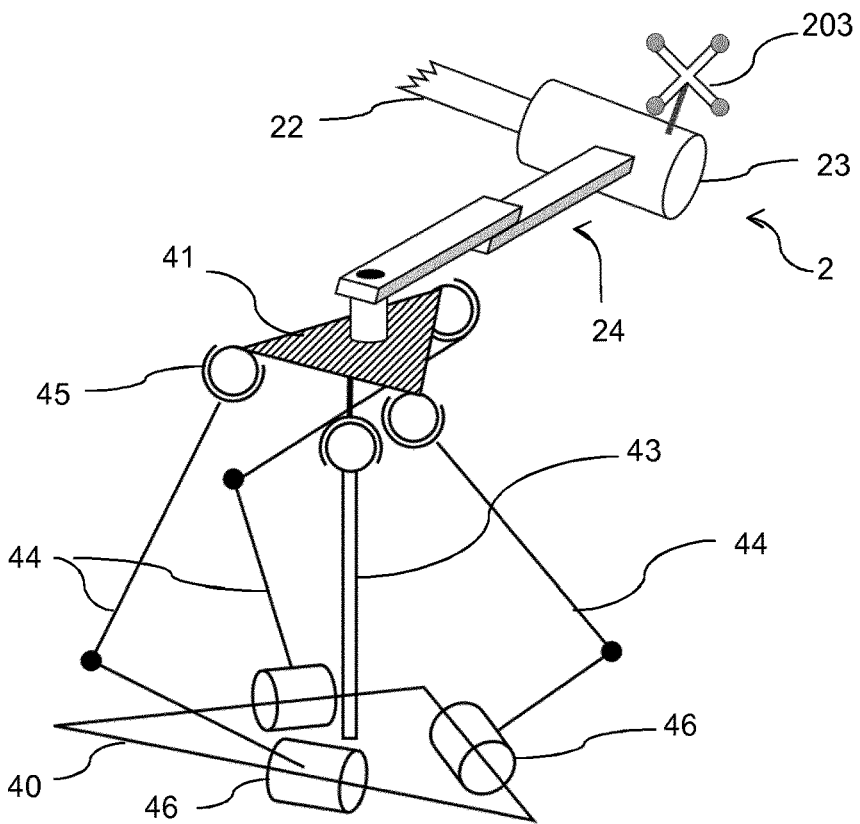
FIG. 5 shows a schematic representation of another embodiment of a parallel architecture.

FIGS. 4 and 5 show two other possible and non-limitative embodiments of a parallel architecture.

In the embodiment of FIG. 4, the base 40 is connected to the platform 41 by four segments 43, 44. One segment 43 has a fixed length and is rigidly attached to the base 40; the three other segments 44 are connected to the base 40 and comprise a linear motor providing a translational degree of freedom of each respective segment. Each of the four segments 43, 44 is connected to the platform 41 by a respective ball joint 45.

In the embodiment of FIG. 5, the base 40 is connected to the platform 41 by four segments 43, 44. One segment 43 is linear with a fixed length and is rigidly attached to the base;

the three other segments 44 comprise an articulation (e.g. pivot link). These three segments 43 are connected to the base 40 by a respective motorized pivot link 46 providing a rotational degree of freedom of each respective segment, and are connected to the platform 41 by a respective ball joint 45.

It should be noted that the actuation unit may comprise a first portion having a parallel architecture as described above, and a second portion that does not have a parallel architecture, thereby mixing parallel and serial architectures. The actuation unit comprises from three to five motorized degrees of freedom; the portion with the parallel architecture comprises at least two of said motorized degrees of freedom.

It can be seen in FIGS. 3 to 5 that the cutting tool 2 is coupled to the platform 41 of the actuation unit by a planar mechanism 24 that will be described in more detail below. More generally, in case of a mixed architecture of the actuation unit, the planar mechanism is mounted on the terminal part (which may or may not be the platform) of the actuation unit.

As it will be explained in more detail below, the actuation unit 4 is controlled by the control unit 300. The control unit may be integrated in the robotic device, or remote from the robotic device.

The cutting tool is coupled to the actuation unit by a planar mechanism designated under reference 24 throughout the set of drawings, the planar mechanism being configured to constrain the movement of the cutting tool within the cutting plane. Thanks to this planar mechanism, the user remains free to move the cutting tool within the target plane, thereby enjoying his/her usual feeling when accomplishing the surgical gesture. This also provides for a greater safety of use of the robotic device, since the user's intervention is always required to perform the cut.

Advantageously, the cutting tool can be decoupled from the planar mechanism. Preferably, especially in the case where the cutting tool is not intended to receive a tracker, the attachment means for the cutting tool provides reproducible fixation.

Several different architectures exist to implement a planar mechanism. For example, the planar mechanism can be made of only one rotation axis and then one translation axis that carries the cutting tool along its longitudinal direction. Alternatively, the planar mechanism can be made of two orthogonal translation axes and then a rotational axis. According to another embodiment, the planar mechanism can be a slider in the form of an arch, including a rotation axis, and then a translation axis that carries the cutting tool.

According to an embodiment, the planar mechanism 24 is passive, meaning that the mechanism is not motorized and can be freely manipulated by the user. For example, in the embodiment shown in FIG. 3, the passive mechanism 24 comprises segments 24a-24d linked by three parallel rotation axes 24e-24g which are orthogonal to the cutting plane. One advantage of such a passive mechanism is to preserve all the perceptions of the user when the saw is manipulated in the bone. For example, surgeons are used to freely manipulate a saw in a cutting block and to detect when the saw blade has reached the back of the bone by sensing changes in the bone resistance, and this perception is fully preserved with a passive planar mechanism that has very low friction at its joints.

Alternatively, the planar mechanism may also be at least partially active, i.e. comprising at least one motorized degree of freedom. If the planar mechanism is active, i.e. it comprises at least two motorized degrees of freedom, the cut(s) can be performed automatically. It is to be noted that said motorized degrees of freedom are all configured to move the cutting tool within the cutting plane.

Whatever the embodiment, the planar mechanism may comprise a locking system for locking each of its degrees of freedom once the cutting plane has been aligned with the target plane.

It is possible to make the actuation unit and planar mechanism sterile components, to be sterilized before each intervention. But, in a preferred embodiment, the actuation unit with its cables and equipped with the planar mechanism are covered by a single-use sterile drape. Additional components of the system can be also protected under the sterile drape. This has the advantage of facilitating and reducing cost of manufacturing and design, but also of being used easily for multiple consecutive surgeries without requiring re-sterilization of the device. The cutting tool itself is sterile, like any conventional surgical tool. Typically, it is sterilized before each intervention using autoclave. Different types of mechanical adaptors between the sterile drape and the cutting tool can be provided. Such adaptor does not require a very precise reproducible fixation if the cutting tool contains a tracking element (described in more detail below), which increases the accuracy of the global system. The sterile drape covers the planar mechanism to facilitate the design and manufacturing of the device. For example, this design allows using ball-bearings mechanisms that would be difficult to autoclave.

The system comprises an articulated lockable holding arm 5 supporting the actuation unit and suited to be connected to a mechanical support such as an operating table, a leg holder or mounted on a mobile cart which wheels can be blocked. A leg holder is an adjustable mechanism configured to maintain the leg in a given flexed position when the patient lies on the operating table.

The holding arm is made of several articulated segments using ball joints, rotational and/or translational joints.

The holding arm is lockable, either manually by a knob (mechanical locking system) or actively by a dedicated actuator of a locking system. The locking system may be an electrical system, a piezoelectric system, a hydraulic system, a pneumatic system or a combination of such systems (e.g. a hydraulic cylinder driven by an electric motor). For example, company SMITH & NEPHEW sells a passive holding arm, actively lockable, named SPIDER™. The actuator can be a button, a foot switch, a remote button, etc. To manipulate the robotic device, the user has to maintain the actuator activated until the desired pose of the robotic device has been achieved.

The holding arm supports the weight of the robotic device and maintains it in a rough positioning relative to the anatomical structure to be treated. It limits the movements of the user when operating the device—and, in advantageous embodiments, also damps movements of the user and/or the patient, vibrations of the cutting tool and reaction forces caused by movements of the actuation unit.

According to an embodiment, the holding arm is passive.

Advantageously, the holding arm may be braked progressively depending on the distance between the robotic device and a target position of the robotic device relative to a tracker fixed to the patient. For example, the braking force may be inversely proportional to the distance of the robotic device to its target position. Alternatively, one or several concentric volumes (e.g. cubes or spheres) may be defined around the target position of the robotic device. The braking force may adjust depending on the presence of the robotic device in one of said volumes. Thus, when the robotic device is close to the target position, the holding arm is braked and the user may receive a force-feedback information. Alternatively, feedback information may be provided in the form of a light or acoustic signal. For example, a variable flash frequency and/or intensity of a light signal may indicate the distance between the robotic device and its target position. Similarly, a variable frequency, repeat speed and/or amplitude of an acoustic signal may indicate such a distance. In any case, the braking is not full, so that the user is always able to manipulate the robotic device until its final desired position. The holding arm is then locked upon an action from the user (e.g. by operating the actuator, e.g. releasing or pushing a button). If the user wants to move the robotic device again, he/she has to operate the actuator again, which frees the holding arm—possibly with a braking force as described above. If a new target position of the robotic device is defined, new braking volumes are defined, and the braking is adjusted based on said new volumes.

In an embodiment, the holding arm is equipped with weights to counterbalance the weight of the control unit, as it is commonly used for carrying and placing microscopes in the surgical field for example.

In an embodiment, the holding arm has a vertical translation with a spring mechanism to compensate for the weight of the global system, then it has a serial architecture with a large planar structure made of three parallel and vertical axes. Each axis is equipped with a locking system.

Figure 6:
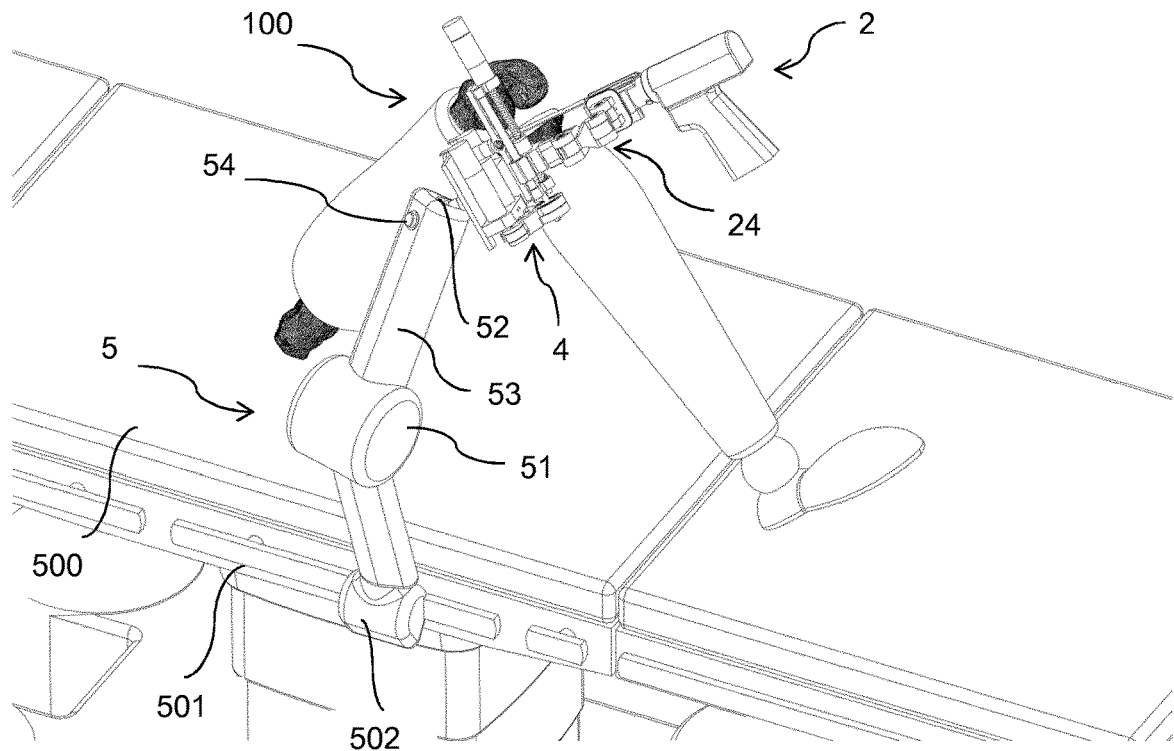
FIGS. 6 and 7 represent embodiments of a holding arm carrying the robotic device.

FIG. 6 illustrates an embodiment of the holding arm 5, which is fixed to a rail 501 of the operating table 500 by a clamp 502. The holding arm is formed of the following kinematic links, in a sequence starting from the clamp: a pivot link 51 and a ball joint 52. One of the segments 53 of the holding arm is provided with an actuator 54 that allows unlocking the holding arm when pushed. Advantageously, the actuator is located in a upper part of the holding arm so as to manipulate the arm and the robotic device easily in case the user wants to change the position of the robotic device relative to the anatomical structure.

Figure 7:
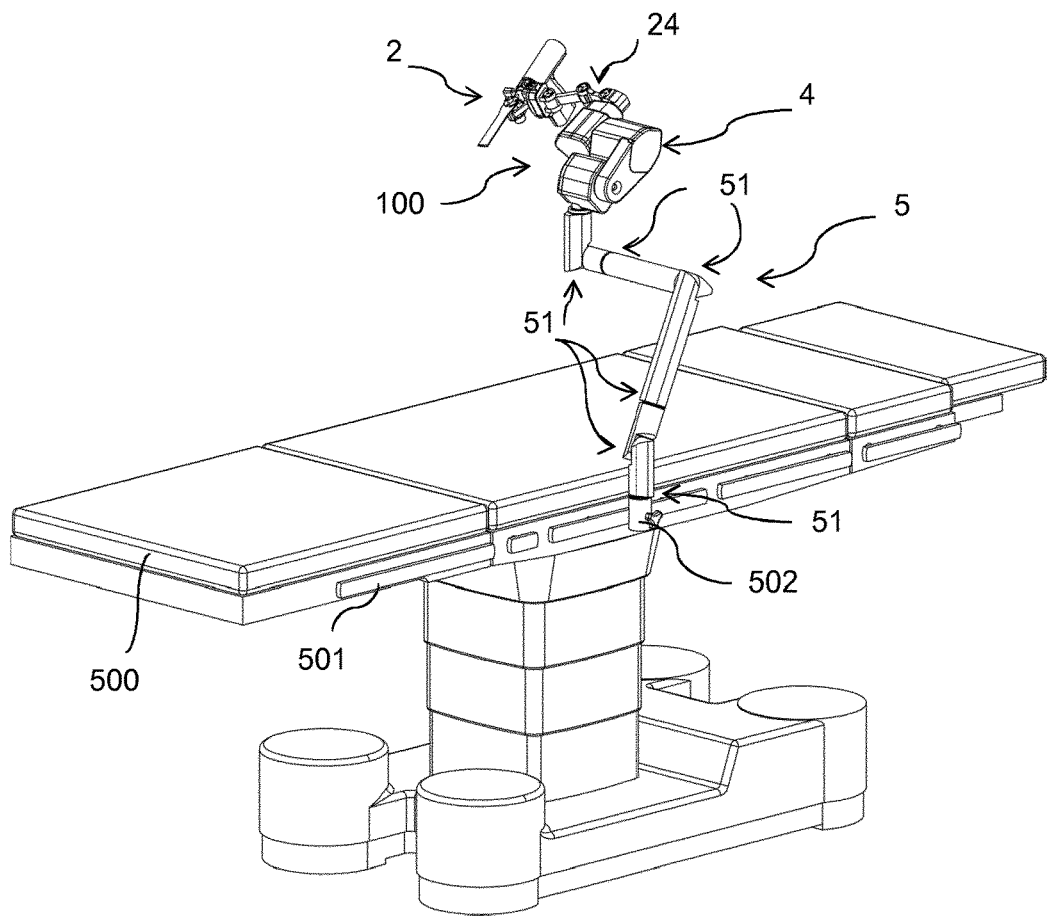

FIG. 7 illustrates another embodiment of the holding arm 5, which is fixed to a rail 501 of the operating table 500 by a clamp 502. The holding arm is formed of six pivot links 51. The holding arm may be locked by an actuator (not shown).

Preferably, the connection between the holding arm and the actuation unit is as close as possible to the base of the actuation unit or to the center of gravity of the robotic device in order to minimize any lever-arm effect. Preferably, the base 40 of the actuation unit 4 is fixed to the holding arm.

According to an embodiment, the device may further comprise a support unit configured to create a partial mechanical link between the actuation unit and the anatomical structure. The support unit may be attached directly or indirectly to the holding arm or to the base of the actuation unit. The support unit is usually a sterile component. The connection between the support unit and the actuation unit or the holding arm can be established on the sterile drape via an intermediate part (not shown) if the actuation unit is covered with a sterile drape. In case the robotic device is sterile, the support unit can be connected directly to the robotic device.

If a support unit is used, it is arranged so as not to hinder the movements required to carry out the surgical intervention. In particular, the support unit is arranged so as not to interfere with the movements of the robotic device to implement each cut.

Generally, the support unit comprises at least one element intended to be in contact with an anatomical structure (the anatomical structure to be cut or an anatomical structure adjacent thereto, e.g. the soft tissues surrounding a bone to be cut). This element can be attached to the patient by at least one strap. According to a preferred embodiment, this element may comprise at least one slot through which the strap extends. The strap can be flexible or semi-rigid (e.g. like fastening device for ski boots). The strap can be adjusted by any suitable means, such as fastening mechanisms, hoop-and-loop fasteners (also known as Velcro™), etc. Alternatively, the strap can be adhesive, or comprises at least one portion made of a high-friction coefficient material (e.g. soft thermoplastic, silicone) placed in contact with the anatomical structure.

Besides, the support unit comprises a mechanical connection between the base of the actuation unit (or the holding arm) and the element of the support unit which is in contact with the anatomical structure. The connection can be activated when the robot is in use and deactivated when the surgeon needs to move the leg or to move the robotic device in order to carry out another cut. According to an embodiment, said connection may be rigid. Alternatively, said connection can be articulated and lockable in at least one degree of freedom to adjust the distance between the robotic device and the patient, or to take into account the patient's morphology. Once the robotic device has been placed in the desired position and orientation, some degrees of freedom may remain free, provided that the support unit still allows limiting movements and vibrations of the anatomical structure relative to the actuation unit. This mechanical connection may be made of at least two parts detachable from one another, for example using a rapid fixation, latch or magnets. A first part is attached to the element of the support unit in contact with the anatomical structure; a second part is attached to the base of the actuation unit or to the holding arm. Thus, the actuation unit or the holding arm may be disconnected from the anatomical structure simply by releasing the mechanical connection, without any need to dismount the support unit from the patient. This is particularly useful in case the user wants to change the position or flexion of the leg during the intervention, e.g. in view of checking the ligament balancing or the postoperative alignment of the leg, or in case the user needs to move the robotic device, e.g. to correct an unsuitable positioning or to carry out another cut.

Optionally, the support unit may include, in combination with the above described components, one or several rods intended to be in contact with the anatomical structure. For example, in the case of TKA, such a rod could be in contact with the epicondyle. Said rod can be rigid or damped (using a spring member). Thus, without being rigidly attached to the bone, said rod allows maintaining a distance between the anatomical structure and the robotic device when the above-described strap is tightened in a determined direction.

In addition to or instead of the rod(s), the support unit may comprise at least one (active or passive) suction pad intended to stay in place on an anatomical structure (bone, skin or other soft tissue) in case of relative movement of the robotic device and the anatomical structure, and also to provide damping.

In a preferred embodiment, the support unit is attached around the body part containing the anatomical structure.

For example, when the body part is the leg, the support unit may be attached to the tibia or to the femur. The support unit may also be attached to both the tibia and the femur; in this case, the support unit is advantageously articulated so as to enable moving the leg (in particular adjusting the flexion of the leg) without removing the support unit.

The support unit acts as a stabilizer. Said support unit may be rigid, damped (e.g. spring-loaded) and/or provide adjustable damping properties. The contact between the support unit and the patient's body may be made of one or several points or of at least one surface.

Advantageously, the support unit may remain in the same position relative to the patient when a plurality of cuts is being implemented. However, since the degrees of freedom of the platform in orientation and in translation are quite small (typically, ±15° and ±30 mm, respectively), it may be necessary to reposition the support unit in order to carry out a new cut.

The system also comprises a tracking unit 200 configured to determine in real time the pose of at least one of the cutting tool with respect to the anatomical structure to be cut.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination. According to a preferred embodiment, the tracking system is based on passive optical technology.

The tracking unit comprises at least one tracker that may be attached to any component of the actuation unit, e.g. to one of the mobile segments.

The position of the platform of the actuation unit is known in real time thanks to encoders or sensors of the motors, and a calibrated model of the actuation unit that includes all axes and distances of the actuation unit. Using this model, and well-known geometric modeling techniques in robotics, it is possible to calculate the relative positions of all segments, so if one measurement is known in a coordinate system attached to the base of the actuation unit using an external tracker, then other component of the actuation unit is also known in the same coordinate system. Additionally, if a tracker is attached to the base of the actuation unit and a second tracker is attached to the anatomical structure, then the pose of any component of the actuation unit is known in the coordinate system attached to the tracker of the anatomical structure.

According to an embodiment, no tracker is attached to the cutting tool. In this way, the cutting tool does not bear the weight of the tracker and the region of operation of the cutting tool is freed from the tracker.

However, if the planar mechanism coupling the cutting tool to the actuation unit is passive, only the pose of the plane of the planar mechanism and of the connection between the planar mechanism and the last component of the actuation unit (e.g. the platform) can be determined. In other words, the pose of the saw itself relative to the actuation unit cannot be precisely known. Note that this problem may be avoided with a planar mechanism that comprises encoders, since the position of each segment of the active planar mechanism and of the saw can thus be determined.

In another and preferred embodiment, a first tracker is attached to a component of the actuation unit (e.g. the base) and a second tracker is attached to the cutting tool in order to offer a redundant and more accurate measurement of the cutting tool position and orientation for safety purpose, taking into account any mechanical backlash that may exist between the actuation unit and the cutting tool.

In addition, at least one tracker is rigidly attached to the patient's anatomical structure to be cut so as to allow localizing the cutting plane relative to the coordinate system of this anatomical structure to be cut.

Throughout the set of drawings, the tracker attached to the cutting tool is designated by reference 203.

In case no tracker is attached to the cutting tool, the compensation of relative motion between the robotic device and the anatomical structure may be implemented as follows.

During the cut, the actuation unit displaces the planar mechanism so that the cutting plane coincides with the target plane. The pose of the robotic device is updated at a high frequency, considering the positions of the base of the robotic device and the anatomical structure.

To that end, if the cutting plane is parallel to the plane of the planar mechanism, one solution is to use the geometrical model of the robotic device to determine the new position of the actuation unit (motors) that would make the plane in which the planar mechanism moves and the target plane coincide. Said geometrical model may be known from the CAD model of the actuation unit, or from a dedicated calibration step, using well known geometric modeling techniques in robotics.

Figure 8:
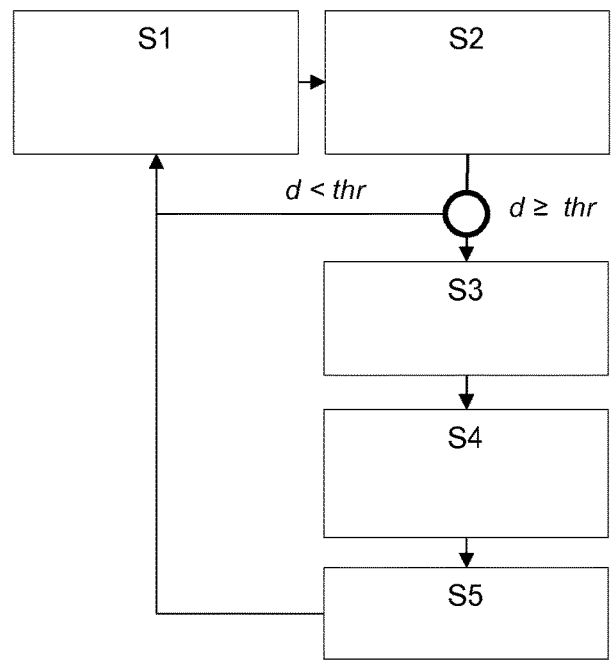
FIG. 8 represents an embodiment of a compensation control loop implemented by the control unit, in case no tracker is attached to the cutting tool.

FIG. 8 is a flowchart describing the control loop allowing the compensation.

In step S1, a new pose of the robotic device and the anatomical structure is determined using localization information provided by the trackers.

In step S2, based on the geometrical model of the robotic device, the theoretical position and orientation of the planar mechanism can be computed from the new pose determined in step S1. Then, a deviation d between the plane of the planar mechanism and the target plane is computed.

If the deviation d is less than a threshold thr, the cutting tool can be operated and a new pose of the robotic device and anatomical structure is determined (step S1).

If the deviation d is greater than or equal to the threshold thr, then in step S3 the target plane is projected in the coordinate system of the robotic device.

In step S4, a new attitude of the robotic device is computed to reach the target plane. This computation determines the movements to be applied by the motors of the actuation unit.

In step S5, the motors of the actuation unit are activated in accordance with step S4.

Then, the new position of the robotic device and anatomical structure is determined (step S1).

However, this procedure relies solely on the geometrical model of the robotic device, which is never perfect due to mechanical backlashes and irregularities, as well as structural deformations that are changing depending on the relative positions of the cutting tool and the various parts of the robotic device.

Another issue is that the planar mechanism itself may slightly bend. As a result, its components do not have the same position and orientation. Indeed, a variable shift on the position and orientation of the planar mechanism is observed, and the compensation of the cutting tool position is never perfect, preventing the robotic device from converging to the target plane. In such case, either the robotic device oscillates, or it converges to a position which is shifted from the target plane.

To improve motion compensation, an additional tracker may be rigidly attached to the cutting tool. This additional tracker allows determining reliably the position and orientation of the cutting tool in the coordinate system of the robotic device.

Instead of attaching said additional tracker to the cutting tool, it is possible to rigidly attach it to the end of the planar mechanism opposite the actuation unit. Said end of the planar mechanism may comprise an interface capable of receiving any type of cutting tool as mentioned above (sagittal saw, reciprocal saw, burr . . . ) but also other surgical tools such as a drill guide to be used to drill the pegs for implanting the prosthesis, and/or a cutting guide, etc. For example, the drill guide can have a toothed end intended to grip into the surface of the anatomical structure where a hole has to be drilled. Advantageously, a handle is provided at the opposite end of the drill guide to facilitate its manipulation by the surgeon. Thus, once the toothed end has been applied to the anatomical structure, the surgeon can simply change the orientation of the drill guide thanks to a navigation interface. The drill may carry a tracker, instead of having the tracker carried by the end of the planar mechanism.

The compensation of relative motion between the robotic device and the anatomical structure using the additional tracker rigidly attached to the cutting tool or to the end of the planar mechanism may be implemented as follows.

The control loop described with reference to FIG. 8 is thus changed to the control loop shown in FIG. 9.

In the improved control loop, the actual position of the cutting tool or of the end of the planar mechanism is used instead of the theoretical position of the planar mechanism.

This greatly increases the confidence in the compensation mechanism.

Moreover, the association of the tracker attached to the cutting tool and the tracker attached to the actuation unit enables dynamic estimation of the alignment error between the two. This alignment error is then used to correct the position and orientation of the planar mechanism to the target plane.

Figure 9:
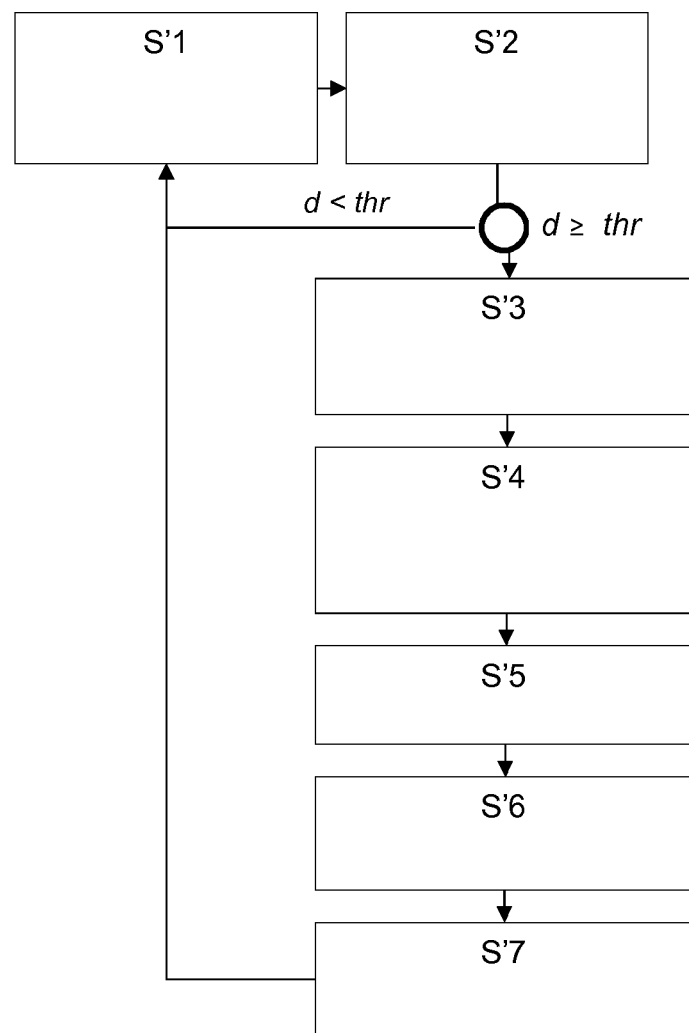
FIG. 9 represents another embodiment of a compensation control loop implemented by the control unit, in case a tracker is attached to the cutting tool.

FIG. 9 is a flowchart describing the control loop allowing the compensation.

In step S'1, new poses of the robotic device, the cutting tool and the anatomical structure are determined using localization information provided by the trackers.

In step S'2, a deviation d between the plane of the cutting tool (cutting plane) and the target plane is computed.

If the deviation d is less than a threshold thr, the cutting tool can be operated and a new pose of the robotic device and anatomical structure is determined (step S'1).

If the deviation d is greater than or equal to the threshold thr, then in step S'3 the plane of the cutting tool (cutting plane) and the target plane are projected in the coordinate system of the robotic device.

In step S'4, a correction matrix $T_{err}$ corresponding to a rigid transformation between the plane of the planar mechanism and the plane of the cutting tool is computed.

In step S'5, the target plane is updated with $T_{err}$.

In step S'6, a new attitude of the robotic device is computed to reach the target plane. This computation determines the movements to be applied by the motors of the actuation unit.

In step S'7, the motors of the actuation unit are activated in accordance with step S'6.

Then, the new position of the robotic device and anatomical structure is determined (step S'1).

From this base algorithm, further improvements have proven to enhance the behavior of the robotic device:

- spatially filtering the positions of the various elements (for instance thanks to a Kalman filter or equivalent);
- averaging the estimation of $T_{err}$ in a given time frame, for instance thanks to quaternion averaging techniques. This allows reducing the potential oscillations due to small inconsistencies between the transformation estimation and the more complex reality of the mechanical links.

The correction matrix $T_{err}$ may vary depending on the current extension of the planar mechanism and therefore it is not constant. It also depends on the mechanical backlash and flexion of the planar mechanism, the position of the robot, and other factors. The correction matrix is calculated in real time, such that the deviation of $T_{err}$ between two calculations is not significant, considering reasonable motions of the saw by the user. This method of correction is extremely precise and efficient for compensating any mechanical defects, backlash and errors in the model.

Advantageously, the attachment of the trackers to the cutting tool and/or actuation unit is reversible and reproducible.

Once operation of the device has been started by the user, the tracking unit continuously feeds back tracking information to the control unit for recalculation and visualization purposes.

During the use of the device the control unit checks in real time if the cutting tool can be aligned with a target plane. If the robotic device is moved such that the cutting tool cannot be aligned with said target plane—e.g. in case of vibrations, and/or an involuntary movement of the patient, the user interface provides information to the user about the ability to align the cutting plane with the target plane in the current device position and, if appropriate, gives indications on how to reposition the robotic device appropriately.

From time to time, the user interface may thus provide information to the user to guide him or her to reposition the actuation unit in an optimal pose to enable alignment of the cutting plane with a target plane. The user interface may also indicate to the user if all targeted cutting planes can be reached from the current position of the actuation unit, and if not, in which direction to move to reach an optimal position.

Said user interface may be visual and/or acoustic.

Figure 13A:
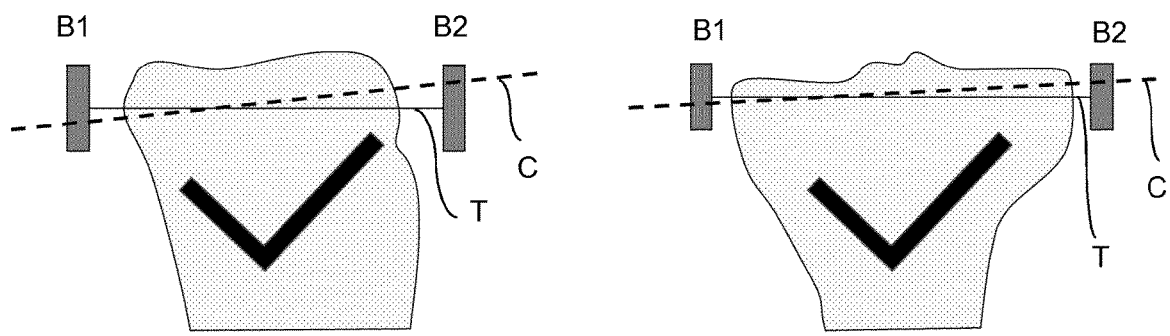
FIGS. 13A and 13B illustrate an embodiment of the user interface for guiding the positioning of the robotic device to align the cutting plane with the target plane.
Figure 13B:
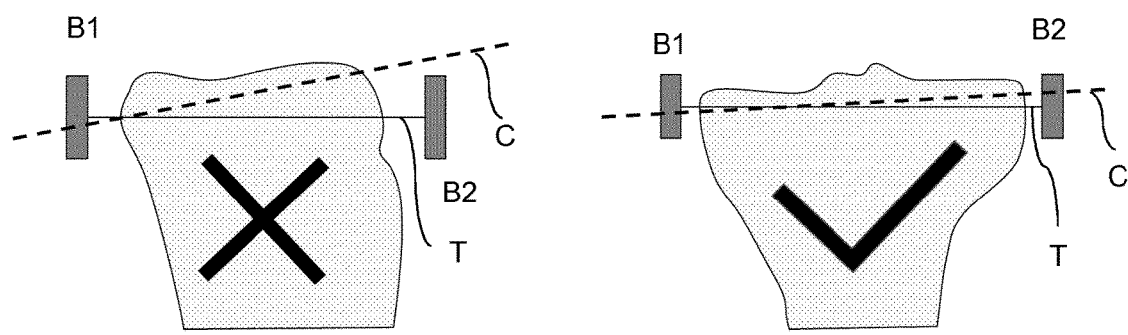

FIGS. 13A-13B illustrate an embodiment of a user interface.

The user interface displays a representation of a part of the anatomical structure to be cut according to two orthogonal views (sagittal on the left, coronal on the right), along with a representation of the target plane (represented by a plain line T) and indicators configured to visually represent the ability of the robotic device to align the cutting plane with the target plane. The representation of the target plane and indicators is computed by the control unit. For examples, the indicators may consist of two bars B1, B2 having a given length, positioned on either side of the anatomical structure. The length of the bars is selected such that, if a line representing the cutting plane (represented by a dotted line C) intersects both of said bars in each of the two views, the actuation unit will be able to align the cutting plane with the target plane without requiring moving the holding arm. This situation is represented in FIG. 13A. To the contrary, if the line C representing the cutting plane does not intersect at least one of the bars B1, B2, in at least one of the views, the actuation unit will not be able to align the cutting plane with the target plane if the base is not moved. The user is thus prompted to unlock the holding arm and move the robotic device until alignment is possible. During this manipulation of the robotic device, the user interface provides guidance to the user, by continuously representing the cutting plane relative to the target plane.

If a realistic 3D model of the anatomical structure is available (i.e. obtained by pre-operative or per-operative imaging of the patient), it may be displayed on the screen, along with a real-time representation of the cutting tool (e.g. envelope of the oscillating blade). For instance, if the cutting tool is a saw, the user can visualize the position of the tip of the saw blade relative to the bone, to ensure that the tip of the saw blade does not exit from the bone. In case the planar mechanism connecting the saw to the actuation unit is motorized, this control may be automated.

According to an embodiment, the user interface may comprise a screen connected to the control unit, e.g. the screen shown on FIG. 2.

According to another embodiment (not shown), the user interface comprises visual indicators such as LEDs. These LEDs may be arranged on a supporting surface that is fixed to the robotic device. Alternatively, the LEDs may be arranged on a support separate from the robotic device and connected to it by a wire. Alternatively, the LEDs may be arranged on a support separate from the robotic device and wirelessly linked to the robotic device. Such a separate support can be placed in the vicinity of the robotic device/cutting tool, in the user's field of view.

Said indicators are intended to instruct the user not to activate the cutting tool, in case the robotic device is not able to compensate for a misalignment between the cutting plane and the target plane. For example, a red and blinking light is turned on as soon as the trackers mounted on the anatomical structure and/or the cutting tool are not visible. It is turned off or changed to a green light as soon as the visibility of trackers is restored.

Another way of providing information to the user is to use numerical displays (e.g. provided by LCD screens) that represent virtual spirit levels. The general orientation of the robotic device can be adjusted by the user based on one virtual spirit level on top of the robotic device and another one on a side (opposite to the patient's leg) of the robotic device. The distance of the robotic device can be adjusted using a support unit, and/or using indicators such as LEDs representing an arrow pointing the desired direction, and/or via the screen of the user interface.

The system further comprises a control unit which is intended to control the pose of the cutting tool in an optimal way in order to align it with a target plane.

According to an embodiment, the control unit may be coupled to the cutting tool used to perform the cut and configured to allow the actuation of the tool only when the cutting plane is aligned with the target plane. This increases safety of the system.

Operation of the control unit will be described in more detail below.

Figure 10:
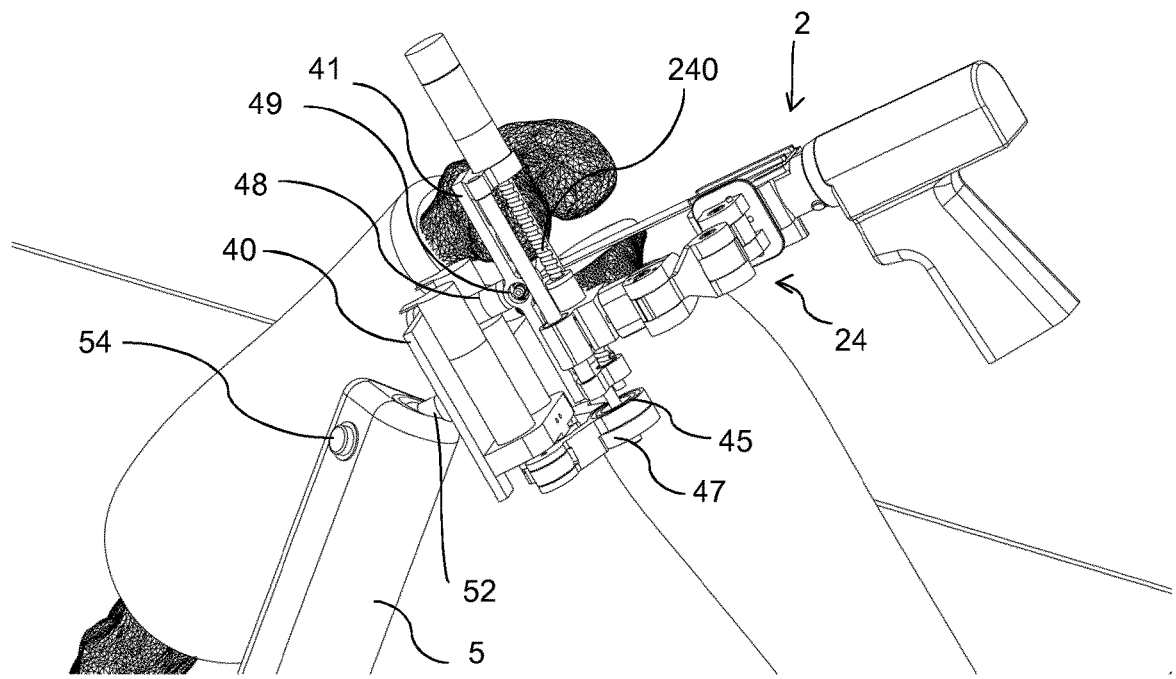
FIGS. 10-11 represent a setup of the robotic device according to an embodiment without any support unit.

FIG. 10 shows an embodiment of a setup of the robotic device according to an embodiment without any support unit.

The actuation unit comprises a base 40 and a platform 41 that is linked to the base by a five bar linkage 47 and a rigid bar 48. The connection between the platform 41 and the five bar linkage is made by a ball joint 45. The connection between the platform 41 and the rigid bar 48 is made by a universal joint 49. This parallel architecture thus comprises two motorized degrees of freedom.

The platform supports a feed axis 240 onto which the planar mechanism 24 is attached, the plane of the planar mechanism being orthogonal to the feed axis. The feed axis allows moving the cutting tool 2 along an axis orthogonal to the plane of the planar mechanism 24, thus providing an additional motorized degree of freedom in translation to the actuation unit.

The base 40 of the actuation device is connected to the end of the holding arm 5. The holding arm can be unlocked by pressing a button 54.

Figure 11:
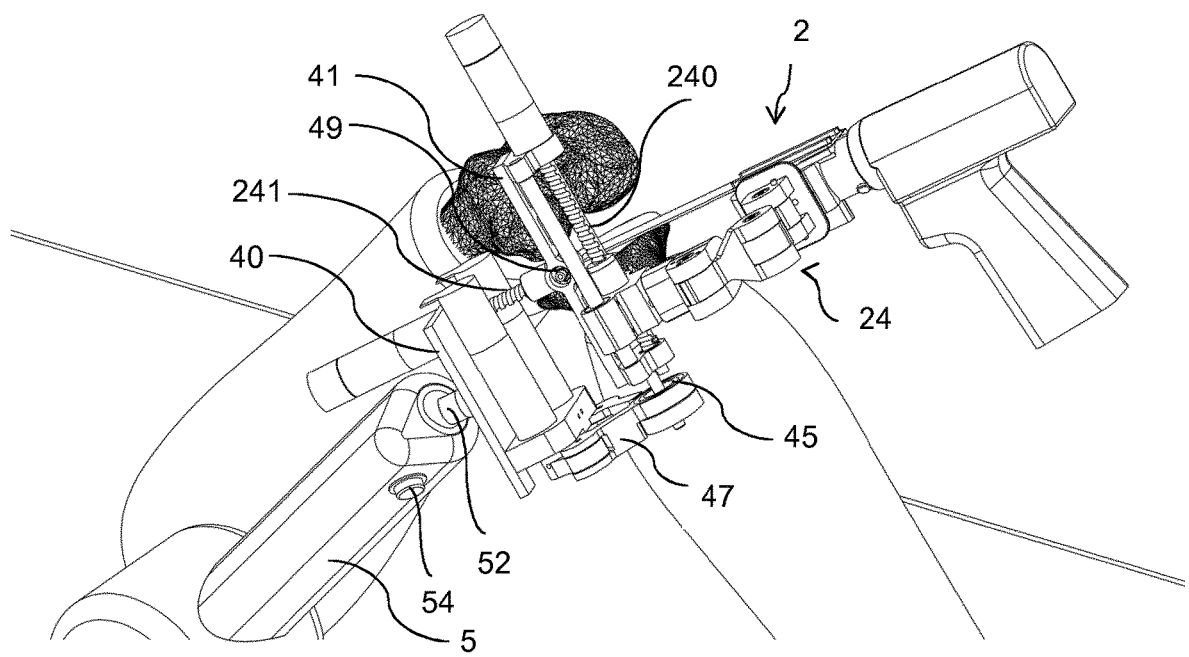

FIG. 11 shows an embodiment of a setup of the robotic device according to an embodiment without any support unit.

As compared to the embodiment of FIG. 10, the actuation unit comprises an additional motorized degree of freedom in translation, in the form of a screw 241 which extends in a plane parallel to the plane of the planar mechanism 24.

Figure 12:
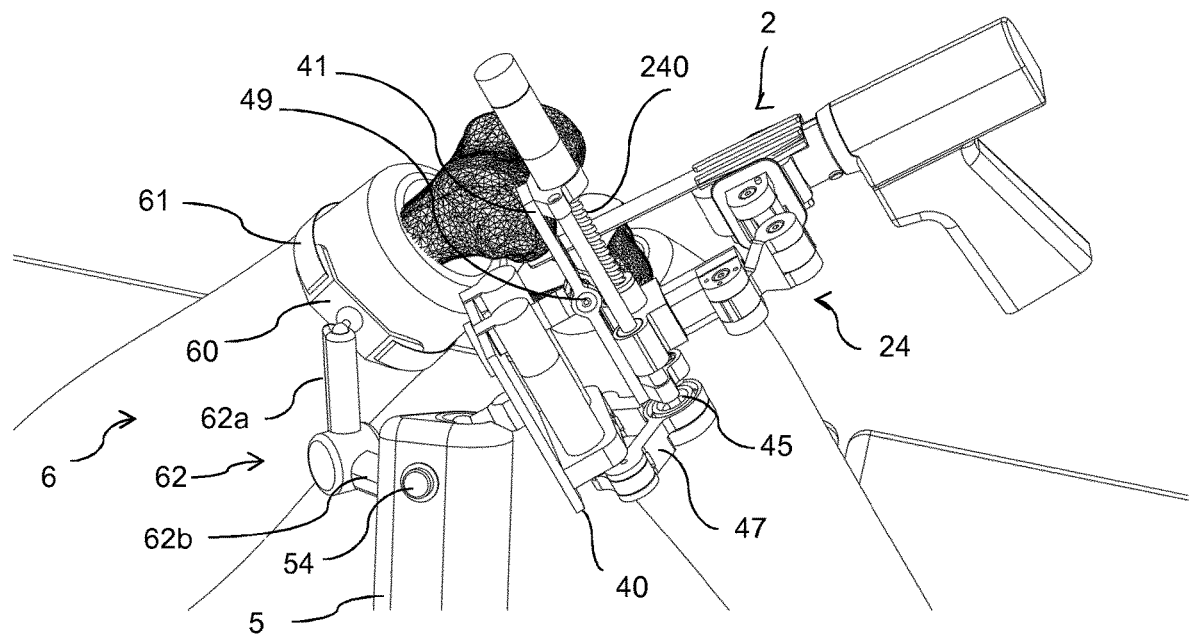
FIG. 12 represents a setup of the robotic device according to an embodiment with a support unit.

FIG. 12 shows an embodiment of a setup of the robotic device according to an embodiment with a support unit.

The actuation unit is similar to the one of FIG. 10.

The support unit 6 is attached to the holding arm 5. The support unit 6 comprises a strap 61 supporting a support 60 from which extends a first fastener 62a, and a connecting member comprising a second fastener 62b cooperating with the first fastener to create a fast and strong connector 62, the connecting member being attached to the holding arm. The flexible strap 61 and rigid support 60 together enwrap the soft tissues around the patient's femur F. The flexible strap 61 allows tightening the rigid support 60 to the leg, the tension of the flexible strap being adjusted depending on the diameter of the patient's leg. Cushions of different thicknesses can be inserted between the rigid support and the patient's skin to adapt to various sizes of the leg. It is also possible to use a spring mechanism to exert a pressure on the side of the rigid support, which provides a variable adjustment to individual patients. Advantageously, the connector 62 has an architecture that is quite similar to that of the holding arm 5, but with smaller dimensions. The connector can be locked in a given position by a locking system and unlocked by an actuator. The locking system may be an electrical system, a piezoelectric system, a hydraulic system, a pneumatic system or a combination of such systems (e.g. a hydraulic cylinder driven by an electric motor). The actuator can be a button, a foot switch, a remote button, etc. Preferably, the actuator 54 that allows unlocking the holding arm can also be configured to simultaneously unlock the connector 62.

Although the trackers illustrated in the figures are optical trackers, it should be noted that any other tracking technology (e.g. electromagnetic) may be used.

It should be noted that the embodiments described above may be combined.

In addition, the holding arm—and, if any, the support unit which only provides a partial mechanical link—does not require any invasive action onto the patient while fully supporting the weight of the robotic device.

Thus, as compared to the large screws and pins that are implanted in the bone (i.e. that penetrate the bone on several centimeters) in document US 2011/0130761, the robotic device according to the invention is not fixed directly to the patient but held by the holding arm which is attached to a component (operating table, leg holder . . . ) non-invasively fixed to the patient, and may only be coupled directly to the patient by non-invasive attachment means (e.g. a strap, etc.).

Micro or macro motions of the robotic device with respect to the anatomical structure to be cut, including slow and fast motions, are compensated within a tolerance range and a given time frame that defines the precision of the device.

Typically, for bone surgery applications, motions in the range of a few tenths of a millimeter need to be compensated to obtain sufficient precision; such a compensation requires ultrafast motion detection and measurement, as well as calculation of the compensation motion to be applied and execution of the desired compensation motion.

Large surgical robots with six degrees of freedom are very stiff but are very cumbersome and expensive; besides, they have a considerable inertia (especially on the first mobile segment), which is not compatible with real time control of the cutting plane. On the other hand, existing small, lightweight robots cannot be used if they are not rigidly attached to the anatomical structure. By contrast, the invention provides a compact, lightweight robotic device that allows real time control of the cutting plane without requiring any invasive fixation to the patient. In addition, the parallel architecture of the actuation unit, which involves only small movements, is very reactive.

Figure 14:
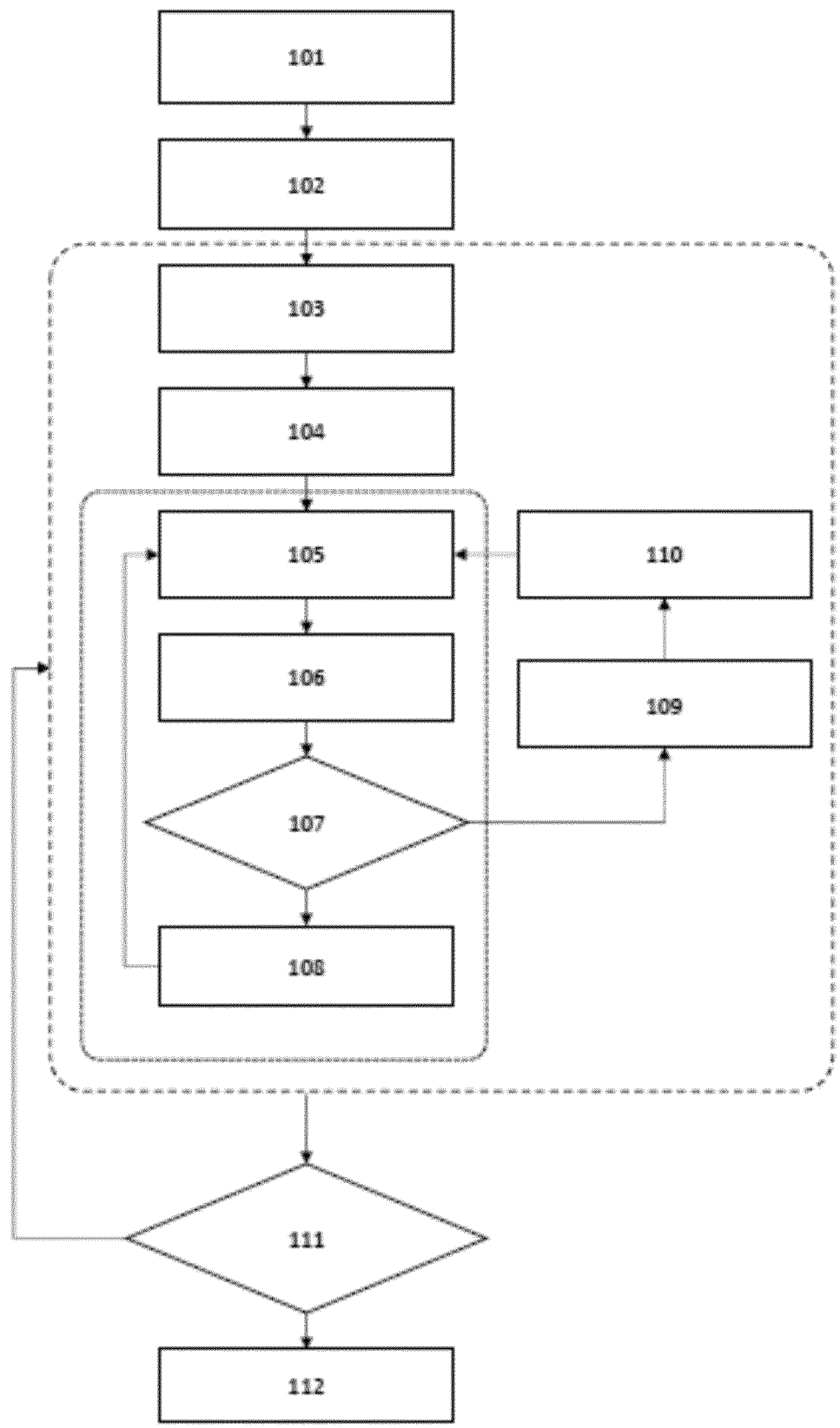
FIG. 14 is a flowchart of a surgical procedure for performing at least one osteotomy implementing an embodiment of the invention.

FIG. 14 is a flowchart of a complete surgical intervention intended to implement at least one osteotomy, such as total knee arthroplasty. It is to be noted that the initial and final steps may not form part of the invention.

In step 101, the patient's anatomy in the region to be treated by the surgical intervention is acquired. Said acquisition may be made, in a manner known per se, for example using imaging means for acquiring an image of the bones and/or a localized pointer (digitization probe) for acquiring a plurality of points of the bone surfaces as it is commonly used in image-free surgical navigation techniques.

In step 102, a surgical planning is carried out based on the acquired patient's anatomy. This planning step results in the definition of the pose of target planes intended to carry out the cuts.

In step 103, the order of the cuts to be carried out is selected. To that end, the control unit retrieves the pose of the corresponding target plane. If several cuts are to be performed, they may be memorized in the system in a specific order, and loaded one after the other. Otherwise, the user interface may allow the user selecting a specific cut. This step may be carried out at any time before step 105.

In step 104, a user positions the robotic device in a rough position intended to allow performing at least the first cut. In this step, the patient's anatomy is also equipped with at least one tracker. The robotic device is also equipped with at least one tracker, so as to allow localizing the relative positions of the robotic device and anatomical structure to be cut.

In step 105, the control unit receives the tracking data of the trackers. Thus, the control unit is able to compute the current position of the robotic device relative to the anatomical structure to be cut.

Based on the current position of the robotic device, the pose of the target plane and the kinematic design of the robotic device, the control computes in step 106 a movement of the actuation unit allowing reaching the target plane. In step 107, the control unit checks whether the target plane is reachable by the robotic device in its current position (i.e. without moving the support unit). If so, the control unit commands the actuation unit to move the cutting tool to the required position so as to have the cutting plane in alignment with the target plane (step 108).

If the current position of the robotic device does not allow achieving alignment on the target plane, the control unit warns the user that he cannot and must not perform the cut (step 109) and computes in step 110 a new position of the robotic device to reach the target plane (said new position implying moving the holding arm and the support unit, if any), and steps 105 to 107 are carried out again.

In step 108, once the cutting plane has been aligned with the target plane, the cut is allowed by the control unit (e.g. by providing an indication to the user that the cutting plane is aligned with the target plane, and/or by allowing the start of actuation of the saw by the user). The user can perform the cut by moving a saw blade within the cutting plane. During this cutting step, the control unit uses the tracking data to check whether the cutting plane remains aligned with the target plane (see the loop between steps 105 and 108).

Once the cut has been completed (after step 108), the user indicates to the control unit that the cut is finished. Said indication can be made for example by pressing a pedal or a button.

In step 111, the user or the control unit checks whether there remain any cuts to be carried out.

If not, postoperative checks may be carried out in step 112.

If cuts remain to be carried out, steps 105-108 (and, if appropriate, 109 and 110) are iterated until all the planned cuts have been carried out.

REFERENCES

WO 2014/198784
US 2011/0130761

The invention claimed is:
1. A surgical system for cutting an anatomical structure of a patient according to a target plane defined in a coordinate system of the anatomical structure, the surgical system comprising:
   a robotic device comprising:
      a cutting tool configured to cut the anatomical structure according to a cutting plane,
      an actuation unit comprising from three to five motorized degrees of freedom, said actuation unit comprising at least one portion having a parallel architecture comprising a base and a platform selectively orientable relative to the base according to at least two of said motorized degrees of freedom, for adjusting a position and orientation of the cutting plane relative to the target plane, wherein the base and the platform are spaced apart by a plurality of interposed legs, wherein each of the legs has a first end pivotally coupled to the base and a second end pivotally coupled to the platform,
      a planar mechanism connecting a terminal part of the actuation unit to the cutting tool,
      a passive articulated lockable holding arm supporting the actuation unit, wherein the holding arm is attached to the base of the actuation unit and the planar mechanism is attached to the platform of the actuation unit,
   a tracking unit configured to determine in real time the pose of the cutting plane with respect to the coordinate system of the anatomical structure,
   a control unit configured to determine the pose of the cutting plane with respect to the target plane, to detect whether the culling plane can be aligned with one target plane without changing the pose of the actuation unit, the control unit being further configured to:
      if the cutting plane cannot be aligned with the target plane, compute an indication to a user to reposition the actuation unit with respect to the anatomical structure, and
      if the cutting plane can be aligned with the target plane, control the actuation unit so as to bring the cutting plane into alignment with the target plane, and
   a user interface coupled to the control unit, configured to indicate directions to a user to position the actuation unit with respect to the anatomical structure according to a pose allowing aligning the cutting plane with the target plane.
2. The surgical system according to claim 1, wherein the culling tool is a surgical saw comprising a saw blade configured to oscillate within the cutting plane.

3. The surgical system according to claim 2, wherein the cutting plane is parallel to a plane of the planar mechanism.

4. The surgical system according to claim 2, wherein the cutting plane is orthogonal to a plane of the planar mechanism.

5. The surgical system according to claim 1, wherein the cutting tool is a burr, a laser, a high-pressure water jet, a scalpel, a lancet, or an ultrasonic cutter adapted for cutting soft tissues.

6. The surgical system according to claim 1, wherein the planar mechanism is passive.

7. The surgical system according to claim 1, wherein the planar mechanism is at least partially active.

8. The surgical system according to claim 7, wherein the planar mechanism comprises at least two motorized degrees of freedom.

9. The surgical system according to claim 8, further comprising a locking system adapted for locking each degree of freedom of the planar mechanism once the cutting plane has been aligned with the target plane.

10. The surgical system according to claim 1, wherein the holding arm comprises a braking system configured to apply a braking force inversely proportional to a distance between a current pose of the robotic device and a target pose enabling alignment of the cutting plane with the target plane.

11. The surgical system according to claim 1, wherein the tracking unit comprises at least one tracker configured to be rigidly attached to the anatomical structure and at least one tracker rigidly attached to the holding arm and/or to the actuation unit.

12. The surgical system according to claim 11, wherein the tracking unit further comprises a tracker configured to be rigidly attached to the cutting tool.

13. The surgical system according to claim 11, further comprising an interface configured for attaching the cutting tool at an end of the planar mechanism, wherein the tracking unit comprises a tracker configured to be rigidly attached to said end of the planar mechanism.

14. The surgical system according to claim 1, wherein the control unit is configured to allow operation of the cutting tool only when the cutting plane is aligned with the target plane.

15. The surgical system according to claim 1, further comprising a support unit connected to the actuation unit and/or the holding arm, the support unit comprising at least one element designed to make contact with the anatomical structure to be cut or a region of the patient's body adjacent to the anatomical structure to be cut so as to provide a partial mechanical link between the cutting tool and the anatomical structure to be cut.

16. The surgical system according to claim 15, wherein the support unit comprises at least two detachable elements, a first element configured to be attached to the anatomical structure and a second element configured to be attached to the actuation unit and/or the holding arm.

17. The surgical system according to claim 16, wherein the first element comprises a rigid base and a strap configured to be wrapped around the anatomical structure to maintain the rigid base, said rigid base being configured to be removably attached to the second element.

18. The surgical system according to claim 16, wherein the first and second elements of the support unit are lockable, and wherein the system comprises a single actuator for unlocking the holding arm and said first and second elements of the support unit.

19. The surgical system according to claim 1, wherein the control unit is configured to implement a control loop comprising:
determining poses of the actuation unit and the anatomical structure using localization information provided by the tracking unit,
based on a geometrical model of the actuation unit, computing a theoretical pose of the planar mechanism from the poses, and computing a deviation between the plane of the planar mechanism and the target plane,
if said deviation is less than a threshold, allowing operation of the cutting tool and determining new poses of the actuation unit and of the anatomical structure,
if said deviation is greater than or equal to said threshold, projecting the target plane in the coordinate system of the actuation unit,
computing a new attitude of the actuation unit to align the cutting plane with the target plane, and determining the movements to be applied by the motors of the actuation unit, and
activating the actuation unit to apply said movements, and determining new poses of the actuation unit and of the anatomical structure.

20. The surgical system according to claim 1, wherein the tracking unit further comprises a tracker and wherein the control unit is configured to implement a control loop comprising:
determining poses of the actuation unit, the cutting tool and the anatomical structure using localization information provided by the tracking unit,
computing a deviation between the cutting plane and the target plane,
if the deviation is less than a threshold, allowing operation of the cutting tool and determining a new pose of the actuation unit, cutting tool and anatomical structure,
if the deviation is greater than or equal to the threshold, projecting the cutting plane and the target plane in the coordinate system of the actuation unit,
computing a transformation between the plane of the planar mechanism and the cutting plane;
updating the target plane with the computed transformation,
computing a new attitude of the actuation unit to align the cutting plane with the updated target plane, and determining the movements to be applied by the motors of the actuation unit, and
activating the actuation unit to apply said movements.

21. The surgical system according to claim 1, wherein the user interface is configured to display a representation of the anatomical structure to be cut, a line representing the target plane and a line representing the cutting plane according to two different views, wherein indicators in the form of a pair of bars have a determined length such that the line representing the cutting plane inter se both bars in each view only if the cutting plane can be aligned with the target plane.

22. A surgical system, comprising:
a cutting tool having an attached tracker;
a passive planar mechanism having a first end connected to the cutting tool;
an actuation unit connected to a second end of the planar mechanism, the actuation unit for adjusting a position and orientation of the cutting tool, wherein the actuation unit has at least three motorized degrees of freedom and comprises a base and a platform selectively orientable relative to the base according to at least two of said motorized degrees of freedom, wherein the base and the platform are spaced apart by a plurality of interposed legs, wherein each of the legs has a first end pivotally coupled to the base and a second end pivotally coupled to the platform;

a passive articulated lockable holding arm, wherein the holding arm is attached to the base of the actuation unit; and the planar mechanism is attached to the platform of the actuation unit; and a control unit configured to:
- determine a pose of the cutting tool using data from sensing of the tracker;
- determine a cutting plane based on the pose of the cutting tool;
- detect whether the cutting plane can be aligned with a target plane for an anatomical structure of a patient without changing the pose of the actuation unit; and
- if the cutting plane cannot be aligned with the target plane, compute an indication to a user to reposition the actuation unit with respect to the anatomical structure; and
- if the cutting plane can be aligned with the target plane; control the actuation unit to bring the cutting plane into alignment with the target plane.

\* \* \* \* \*